US011852643B2

United States Patent
Huang et al.

(10) Patent No.: US 11,852,643 B2
(45) Date of Patent: Dec. 26, 2023

(54) PHYSIOLOGICAL SIGNAL MONITORING DEVICE

(71) Applicant: BIONIME CORPORATION, Taichung (TW)

(72) Inventors: Li-Kang Huang, Taichung (TW); Chun-Mu Huang, Taichung (TW)

(73) Assignee: BIONIME CORPORATION, Taichung (TW)

( * ) Notice: Subject to any disclaimer, the term of this patent is extended or adjusted under 35 U.S.C. 154(b) by 295 days.

(21) Appl. No.: 17/497,549

(22) Filed: Oct. 8, 2021

(65) Prior Publication Data

US 2022/0113323 A1 Apr. 14, 2022

Related U.S. Application Data

(60) Provisional application No. 63/090,814, filed on Oct. 13, 2020.

(51) Int. Cl.
*G01N 1/00* (2006.01)
*G01N 35/00* (2006.01)
*G01N 33/66* (2006.01)

(52) U.S. Cl.
CPC ....... *G01N 35/00732* (2013.01); *G01N 33/66* (2013.01); *G01N 35/00029* (2013.01); *G01N 2035/00039* (2013.01); *G01N 2035/00108* (2013.01); *G01N 2035/00752* (2013.01); *G01N 2800/042* (2013.01)

(58) Field of Classification Search
None
See application file for complete search history.

(56) References Cited

U.S. PATENT DOCUMENTS

| 7,240,565 B2 | 7/2007 | Eisenmann et al. |
| 8,057,753 B2 | 11/2011 | DeAngeli et al. |
| 8,715,571 B2 | 5/2014 | Hanson et al. |
| 10,048,247 B2 | 8/2018 | Bishop et al. |
| 10,139,391 B2 | 11/2018 | Hou et al. |
| 2006/0133956 A1 | 6/2006 | Hamanaka |
| 2009/0041631 A1 | 2/2009 | Cho |
| 2011/0040160 A1 | 2/2011 | Sakata et al. |
| 2012/0143085 A1 | 6/2012 | Sauers et al. |

FOREIGN PATENT DOCUMENTS

| TW | 202025969 A | 7/2020 |
| TW | M599631 U | 8/2020 |

OTHER PUBLICATIONS

Search Report appended to an Office Action, which was issued to Taiwanese counterpart application No. 110137804 by the TIPO dated May 11, 2022 with an English translation thereof.

*Primary Examiner* — Jyoti Nagpaul
(74) *Attorney, Agent, or Firm* — Burris Law, PLLC

(57) ABSTRACT

A physiological signal monitoring device is adapted for monitoring a physiological signal of a biofluid, and includes: a biosensor strip that has at least one signal output end adapted for outputting the physiological signal; a strip reciprocating module that includes a strip seat for receiving the biosensor strip, a guide seat mounted to the strip seat, and a rotating plate mounted rotatably to the strip seat for triggering reciprocating movement of the biosensor strip and the guide seat relative to the strip seat; and a contact module that includes an electronic module, and at least one extending piece connected electrically with the at least one signal output end to transmit the physiological signal to the electronic module.

22 Claims, 35 Drawing Sheets

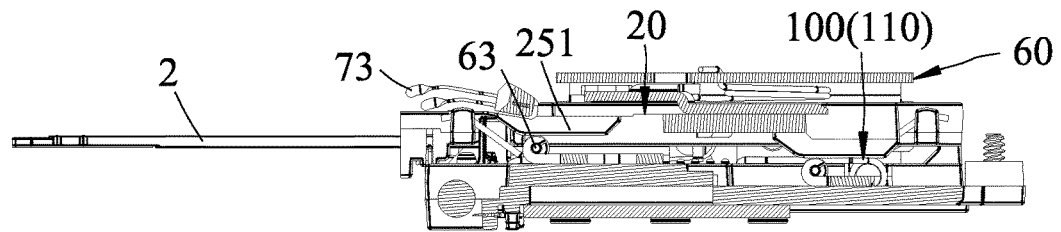
(a)
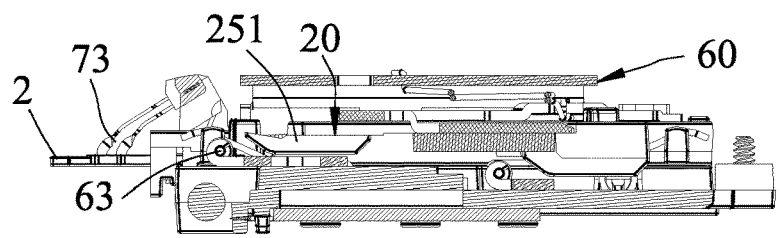
(b)
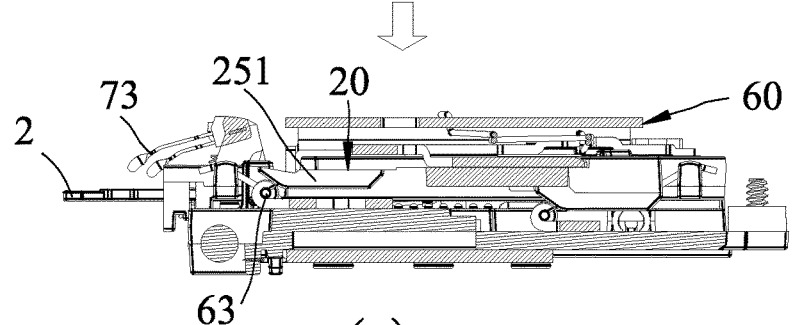
(c)
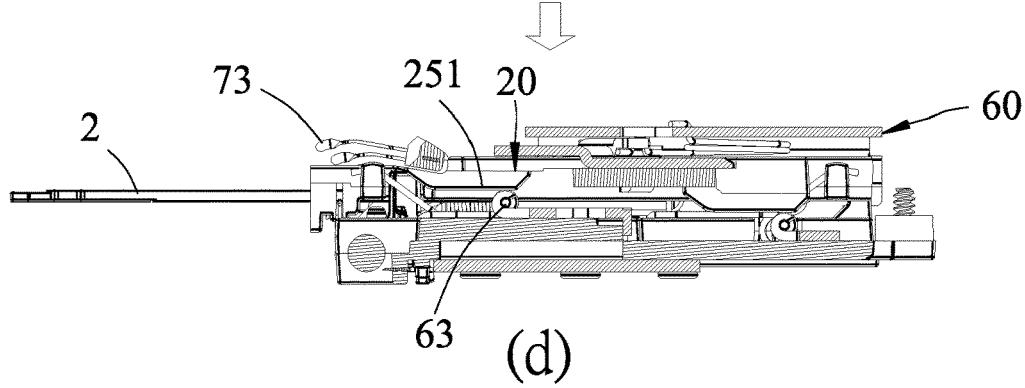
(d)
FIG.31

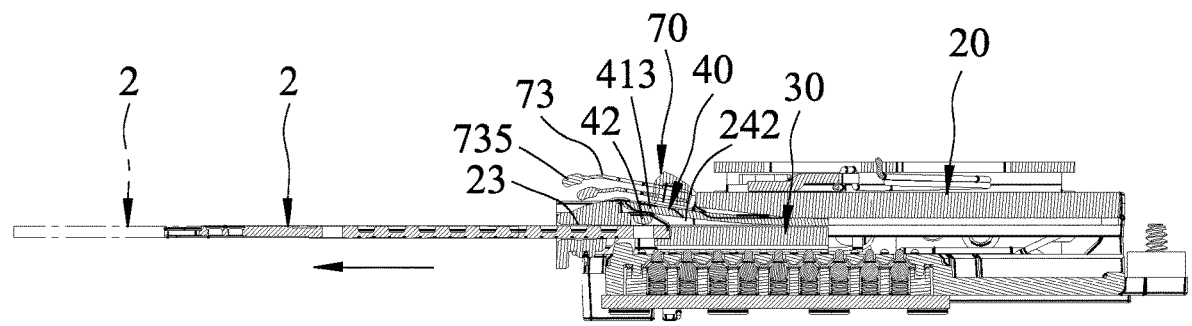
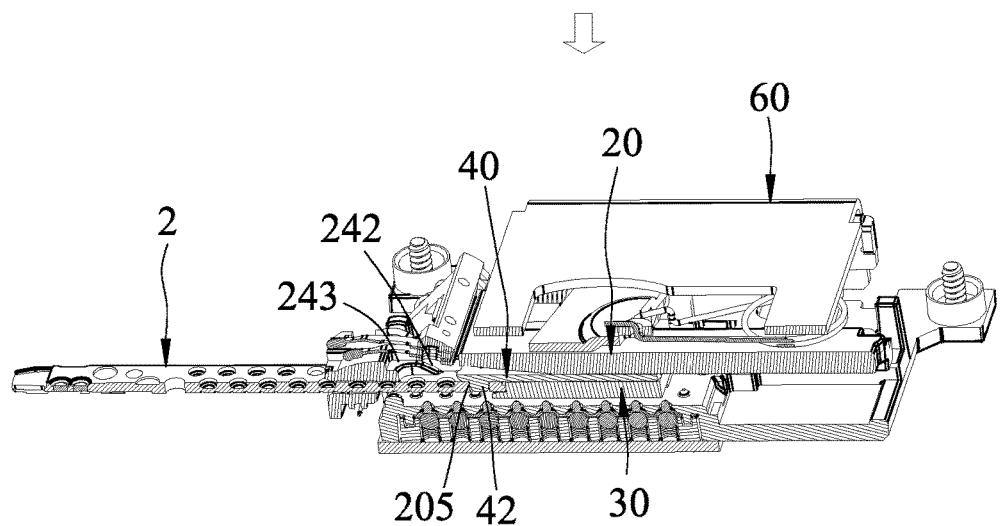
FIG.32

PHYSIOLOGICAL SIGNAL MONITORING DEVICE

CROSS-REFERENCE TO RELATED APPLICATION

This application claims priority of U.S. Provisional Application No. 63/090,814, filed on Oct. 13, 2020.

FIELD

The disclosure relates to a medical device, and more particularly to a physiological signal monitoring device.

BACKGROUND

A conventional trigger mechanism of a blood glucose monitor disclosed in U.S. Pat. No. 7,240,565 B2 for automatically ejecting a test strip uses an actuating spring (34) to drive two control surfaces (30) and two counter surfaces (32) to move relative to each other so as to eject or clamp the test strip. In another conventional trigger mechanism disclosed in U.S. Pat. No. 8,057,753 B2, a memory wire (104) is used to drive the slider (106) to move linearly to eject the test strip. In yet another conventional trigger mechanism disclosed in U.S. Publication No. 20120143085 A1, a push button (46) is used to release a lock to allow a biasing device (48) to drive a contacting portion (40) to push out the test strip. In yet another conventional trigger mechanism disclosed in U.S. Pat. No. 10,048,247 B2, an ejection button (16) is used to drive an actuator arm (32) to swing, thereby driving linear movement of a sled (34) to eject the test strip. In yet another conventional trigger mechanism disclosed in U.S. Pat. No. 8,715,571 B2, an ejection button (16) is used to trigger an actuator arm (32) to drive a sled (36) to move on two guide rails (38,40) to eject the test strip.

On the other hand, a conventional push-to-eject mechanism for ejecting the test strip manually disclosed in U.S. Patent Publication No. 20060133956 A1 uses a first elastic part (111a) to secure the test strip after inserting the test strip. When a slidable moving part (103) is manually operated to push out the test strip, a second elastic part (111b) is used to eject the test strip. In another conventional push-to-eject mechanism disclosed in U.S. Pat. No. 10,139,391, an actuating part (41) of an ejection element (40) is used to push out the test piece when a trigger (42) is manually operated. In yet another conventional push-to-eject mechanism disclosed in U.S. Patent Publication No. 20110040160 A1, an operating body (50) is used to drive a gear (71) to lift and push out a pad portion (65) that carries the biosensor test strip. In yet another conventional push-to-eject mechanism disclosed in U.S. Patent Publication No. 20090041631, an ejection button (11) is used to cooperate with a resilient element (17) to eject the test strip.

However, none of the above-mentioned mechanisms, whether automatic or manual, provides functionalities of automatically inserting, positioning, and ejecting the biosensor test strip.

SUMMARY

Therefore, the object of the disclosure is to provide a physiological signal monitoring device that can automatically insert, position, and eject a biosensor strip.

According to one aspect of the disclosure, the physiological signal monitoring device is adapted for monitoring a physiological signal of a biofluid, and includes a biosensor strip, a strip reciprocating module and a contact module.

The biosensor strip has at least one signal output end that is adapted for outputting the physiological signal.

The strip reciprocating module includes a strip seat that is configured for receiving the biosensor strip, a guide seat that is mounted movably to the strip seat, and a rotating plate that is mounted rotatably to the strip seat. Rotation of the rotating plate is configured to trigger reciprocating movement of the biosensor strip and the guide seat relative to the strip seat.

The contact module includes an electronic module, and at least one extending piece that is electrically connected with the at least one signal output end to transmit the physiological signal to the electronic module.

According to another aspect of the disclosure, the physiological signal monitoring device is adapted for monitoring a physiological signal of a biofluid, and includes a biosensor strip, a strip reciprocating module and a contact module.

The biosensor strip has at least one signal output end that is adapted for outputting the physiological signal.

The strip reciprocating module includes a base body, a strip seat that is mounted to the base body, and that is configured for receiving the biosensor strip, a guide seat that is mounted movably to the strip seat, a rotating plate that is mounted rotatably to the strip seat, and an actuating unit that is mounted movably to the base body. Rotation of the rotating plate is configured to trigger reciprocating movement of the biosensor strip and the guide seat relative to the strip seat.

The contact module is mounted to the base body, is drivable by the actuating unit, and includes an electronic module, and an extending piece that is electrically connected with the at least one signal output end to transmit the physiological signal to the electronic module.

According to yet another aspect of the disclosure, the physiological signal monitoring device is adapted for monitoring a physiological signal of a biofluid, and includes a biosensor strip, a strip reciprocating module and a contact module.

The biosensor strip has at least one signal output end that is adapted for outputting the physiological signal.

The strip reciprocating module includes a base body, a strip seat that is mounted to the base body, that is configured for receiving the biosensor strip, and that includes a driven set, a guide seat that is mounted movably to the strip seat, a rotating plate that is mounted rotatably to the strip seat, and an actuating unit that is mounted movably to the base body, and that includes a driving set. Rotation of the rotating plate is configured to trigger reciprocating movement of the biosensor strip and the guide seat relative to the strip seat. When the actuating unit is moved from the initial position to the securing position, the driven set of the strip seat is driven by the driving set of the actuating unit to move downwardly, thereby moving the strip seat downwardly from an upper position to the lower position, so that the biosensor strip inserted into the strip seat is in contact with the electronic module.

The contact module is mounted to the base body, is drivable by the actuating unit, and includes an electronic module, and an extending piece that is electrically connected with the at least one signal output end to transmit the physiological signal to the electronic module.

BRIEF DESCRIPTION OF THE DRAWINGS

Other features and advantages of the disclosure will become apparent in the following detailed description of the embodiments with reference to the accompanying drawings, of which:

FIGS. 31(a) to (d) are sectional views illustrating the strip seat of the first embodiment being lifted and lowered by an actuating unit;

FIGS. 32(a) and (b) are views illustrating an anchor member of the first embodiment being guided by the strip seat to engage or disengage the biosensor strip;

DETAILED DESCRIPTION

Figure 1:
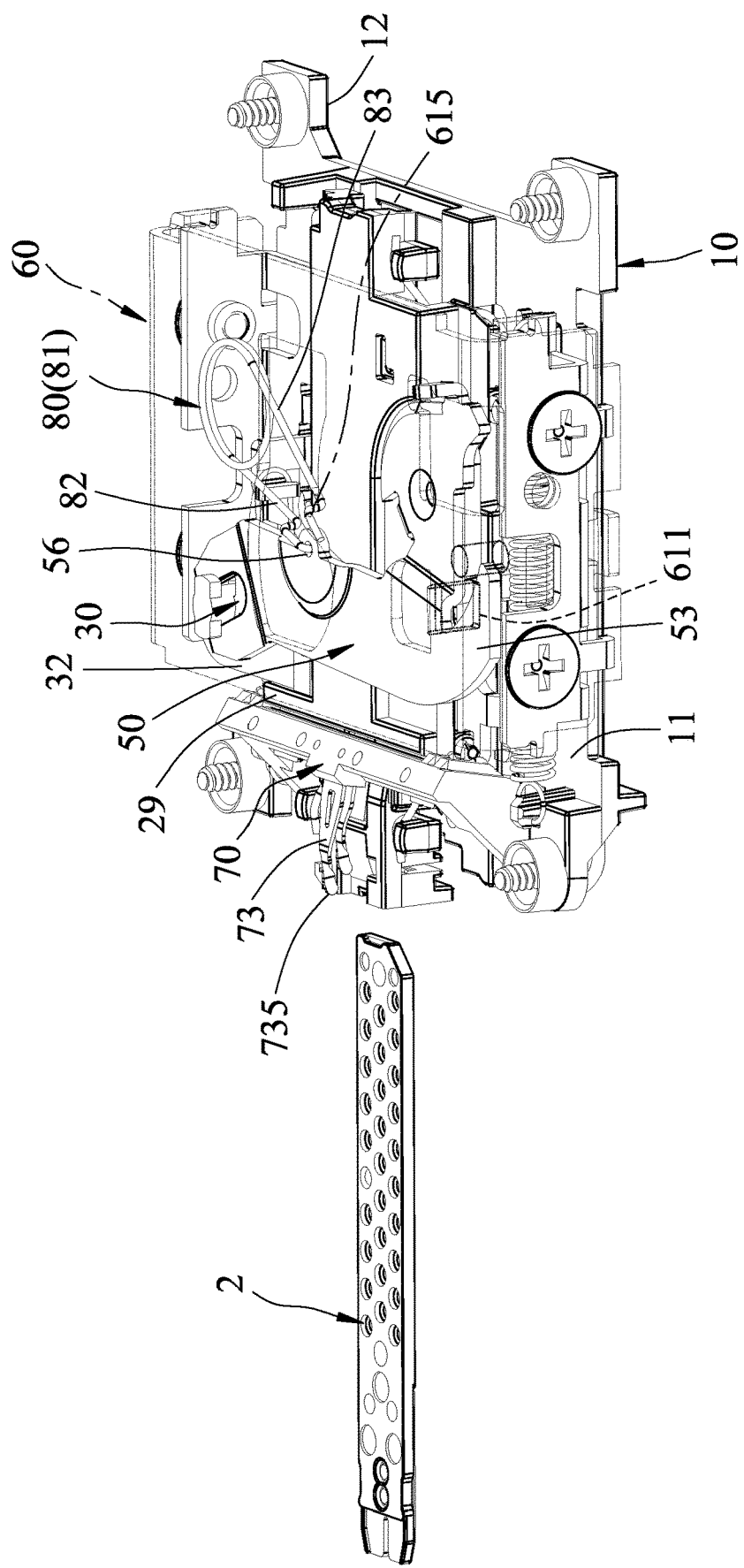
FIG. 1 is a perspective view of a first embodiment of a physiological signal monitoring device according to the disclosure.

Before the present disclosure is described in greater detail, it should be noted that where considered appropriate, reference numerals or terminal portions of reference numerals have been repeated among the figures to indicate corresponding or analogous elements, which may optionally have similar characteristics.

Referring to FIGS. 1 to 4, a first embodiment of a physiological signal monitoring device according to disclosure is adapted for monitoring a physiological signal of a biofluid (not shown). The physiological signal monitoring device includes a biosensor strip 2, a strip reciprocating module, a contact module 70, a first driving spring 80, a second driving spring 90 and a resilient unit 100.

The biosensor strip 2 has an insertion end 201, a conducting end 202 opposite to the insertion end 201, a foolproof edge 203 formed at the insertion end 201, two signal output ends 204 disposed proximate to the conducting end 202, an anchor hole 205 disposed proximate to the insertion end 201, a plurality of code holes 206 disposed between the insertion end 201 and the conducting end 202, and a positioning hole 207 disposed between the signal output ends 204 and the code hole 206.

The strip reciprocating module includes a base body 10, a strip seat 20, a guide seat 30, an anchoring member 40, a rotating plate 50 and an actuating unit 60. The contact module 70 includes an electronic module 1 that has a plurality of code beads 101. It should be noted that the physiological signal monitoring device of the present disclosure is installed in a housing unit (not shown), and the actuating unit 60 thereof is connected to an eject button (not shown) protruding out of the housing unit. The housing unit and the eject button are omitted in the figures for the sake of clear illustration of the embodiment.

The base body 10 of the strip reciprocating module is mounted with the electronic module 1, and has a first end 11, a second end 12, a positioning pole 13, two limit guide portions 14, a plurality of through holes 15, a plurality of guide poles 17, two front stop portions 181, two rear stop portions 182, two pivot poles 19 (only one is visible in FIG. 2), and a stop pole 191. The second end 12 is opposite to the first end 11 in a front-rear direction (X). The positioning pole 13 is disposed on the first end 11, and is configured for engaging the positioning hole 207 of the biosensor strip 2. The limit guide portions 14 extend in the front-rear direction (X), and are disposed between the first end 11 and the second end 12. The through holes 15 are disposed between the limit guide portions 14, and are configured for the code beads 101 of the electronic module 1 to extend therethrough. The guide poles 17 protrude upwardly in a top-bottom direction (Z) perpendicular to the front-rear direction (X). The front stop portions 181 are disposed proximate to the first end 11, and are spaced apart from each other in a left-right direction (Y) perpendicular to the front-rear direction (X) and the top-bottom direction (Z). The rear stop portions 182 are disposed proximate to the second end 12, and are spaced apart from each other in the left-right direction (Y). The pivot poles 19 are disposed at the first end 11. The stop pole 191 is disposed at the second end 12.

Referring to FIGS. 2, 3, 4 and 9, the strip seat 20 of the strip reciprocating module is configured for receiving the biosensor strip 2, is mounted to the base body 10, and is downwardly and upwardly movable, under guidance of the guide poles 17, relative to the base body 10. The strip seat 20 has a top face 21, a bottom face 22, a insertion groove 23, a slide groove 24, a driven set 25, a fool-proof groove 26, a fool-proof spring 261, a first engaging member 27, an engaging hole 281, an arc groove 282, a stop piece 283 and an abutment rib 29.

The bottom face 22 and the top face 21 are opposite to each other in the top-bottom direction (Z). The insertion groove 23 is configured for insertion of the biosensor strip 2 thereinto, and has a front end 231 and a rear end 232 that is opposite to the front end 231 in the front-rear direction (X). The insertion groove 23 and the slide groove 24 are arranged in the top-bottom direction (Z) and are in communication with each other. The slide groove 24 has a straight section 241, a wedge section 242 and a limit section 243. The straight section 241 extends forwardly from the rear end 232 of the insertion groove 23 toward the front end 231 of the insertion groove 23. The wedge section 242 is connected to the straight section 241 and has a height in the top-bottom direction (Z) gradually increasing toward the front end 231 of the insertion groove 23. The limit section 243 is connected to the wedge section 242, and is adjacent to and not in direct communication with the insertion groove 23.

The driven set 25 is disposed outside of the insertion groove 23, and has a plurality of trapezoid pieces 251. Each of the trapezoid pieces 251 has a bottom surface 252 that faces the base body 10, and two inclined surfaces 253 that are opposite to each other in the front-rear direction (X) and that are connected respectively to opposite ends of the bottom surface 252. The fool-proof groove 26 is adjacent to and in communication with the front end 231 of the insertion groove 23. The fool-proof spring 261 is inserted into the front end 231 of the insertion groove 23 (see FIG. 9), and is configured to be resiliently pushed out of the front end 231 of the insertion groove 23 into the fool-proof groove 26 by the fool-proof edge 203 of the biosensor strip 2 during the insertion of the biosensor strip 2 into the insertion groove 23. The first engaging member 27 extends in the front-rear direction (X). The engaging hole 281 extends in the top-bottom direction (Z). The arc groove 282 is disposed around the engaging hole 281. The stop piece 283 is disposed in the arc groove 282. The abutment rib 29 is disposed proximate to the front end 231 of the insertion groove 23, and is elongated in the left-right direction (Y).

The guide seat 30 of the strip reciprocating module is forwardly and rearwardly movable relative to the strip seat 20, and has a seat block 31 mounted to the strip seat 20, and a extension piece 32 connected to the seat block 31. The seat block 31 has a slide portion 310 movably received in the insertion groove 23 of the strip seat 20, a second engaging member 311 disposed above the slide portion 310 and engaging the first engaging member 27 of the strip seat 20, two claw slots 312 formed in the slide portion 310, a carrying platform 313 connected to a front end of the slide portion 310, an inclined guide face 314 formed at the front of the carrying platform 313, and an elongated slot 315 formed in a bottom surface of the slide portion 310 and configured for the code bead 101 of the electronic module 1 to be movably received therein. The extension piece 32 has a first coupling portion 321 extending upwardly and being T-shaped.

The anchoring member 40 of the strip reciprocating module is mounted on the guide seat 30, is co-movable with the guide seat 30 relative to the strip seat 20, and has a claw portion 41 and an anchoring portion 42. The claw portion 41 is slidable along the slide groove 24 of the strip seat 20, and has a positioning end 411 secured to the guide seat 30, a swingable end 412 being opposite to the positioning end 411, and a wedge portion 413 disposed on the swingable end 412. The positioning end 411 has two claws 414 engaging respectively the claw slots 312 of the guide seat 30. The anchoring portion 42 is a hemispherical protrusion protruding from the claw portion 41, and is configured for securing the biosensor strip 2 when the guide seat 30 and the anchoring member 40 are moved rearwardly by the biosensor strip 2 during insertion of the biosensor strip 2. During sliding movement of the anchoring member 40 toward the limit section 243 of the slide groove 24 of the strip seat 20, the swingable end 412 swings under guidance of the wedge section 242 of the slide groove 24 to withdraw the anchoring portion 42 from the insertion groove 23.

The rotating plate 50 of the strip reciprocating module is mounted rotatably to the strip seat 20, and has an engaging member 51, a bent piece 52, a hook portion 53, an abutment portion 54, a second coupling portion 55, a first connecting hole 56 and an upright tab 57. The engaging member 51 rotatably engages the engaging hole 281 of the strip seat 20. The bent piece 52 extends into the arc groove 282 of the strip seat 20, and engages the stop piece 283 of the strip seat 20 to restrain upward and downward movement of the rotating plate 50 along an axis which extends in the top-bottom direction (Z). The abutment portion 54 surrounds the engaging member 51. The second coupling portion 55 is coupled to the first coupling portion 321 of the guide seat 30, and is opposite to the hook portion 53. The first connecting hole 56 is disposed between the hook portion 53 and the second coupling portion 55. The upright tab 57 extends upwardly from a periphery of the abutment portion 54. In the present embodiment, the second coupling portion 55 of the rotating plate 50 is a U-shaped groove engaged rotatably and slidably with the first coupling portion 321 of the guide seat 30. The rotating plate 50 is rotatable between an original position (see FIG. 1) and a rotated position (see FIG. 12). During insertion of the biosensor strip 2, the guide seat 30 is moved rearwardly to drive the rotating plate 50 to rotate in a first rotational direction (D1) from the original position to the rotated position.

The actuating unit 60 of the strip reciprocating module is movable along an axis which extends in the front-rear direction (X) relative to the base body 10. The actuating unit 60 includes an upper actuating seat 61, two lower actuating seats 62 and a driving set 63.

The upper actuating seat 61 is slidable between the front stop portions 181 and the rear stop portions 182 of the base body 10, and has a projecting piece 611, a projecting pin 612, a cutout slot 613, a stop surface 614 and a second connecting hole 615. The projecting piece 611 projects toward the base body 10, and engages the hook portion 53 when the actuating unit 60 is at an initial position (see FIG. 1). The projecting pin 612 projects toward the base body 10, and is proximate to the projecting piece 611. The cutout slot 613 is proximate to the projecting pin 612, and is provided for the upright tab 57 of the rotating plate 50 to extend movably therethrough. The stop surface 614 is disposed next to the cutout slot 613, and is provided for the upright tab 57 of the rotating plate 50 to abut thereagainst. The lower actuating seats 62 are connected to the upper actuating seat 61 and are connected between the base body 10 and the strip seat 20. Each of the lower actuating seats 62 is slidable along the front-rear direction (X), and has two guide tabs 621 slidably engaging a respective one of the limit guide portions 14, and a spring hook 622. The driving set 63 has a plurality of lower driving members 631 connected to the lower actuating seats 62 and being proximate to a corresponding one of the trapezoid pieces 251. In the present embodiment, each of the lower driving members 631 is a roller. When the actuating unit 60 is moved from the initial position to a securing position (see FIG. 14), the driven set 25 of the strip seat 20 is driven by the driving set 63 of the actuating unit 60 to move downwardly, thereby moving the strip seat 20 downwardly from an upper position to a lower position, so that the biosensor strip 2 inserted into the strip seat 20 is in contact with the electronic module 1.

Figure 5:
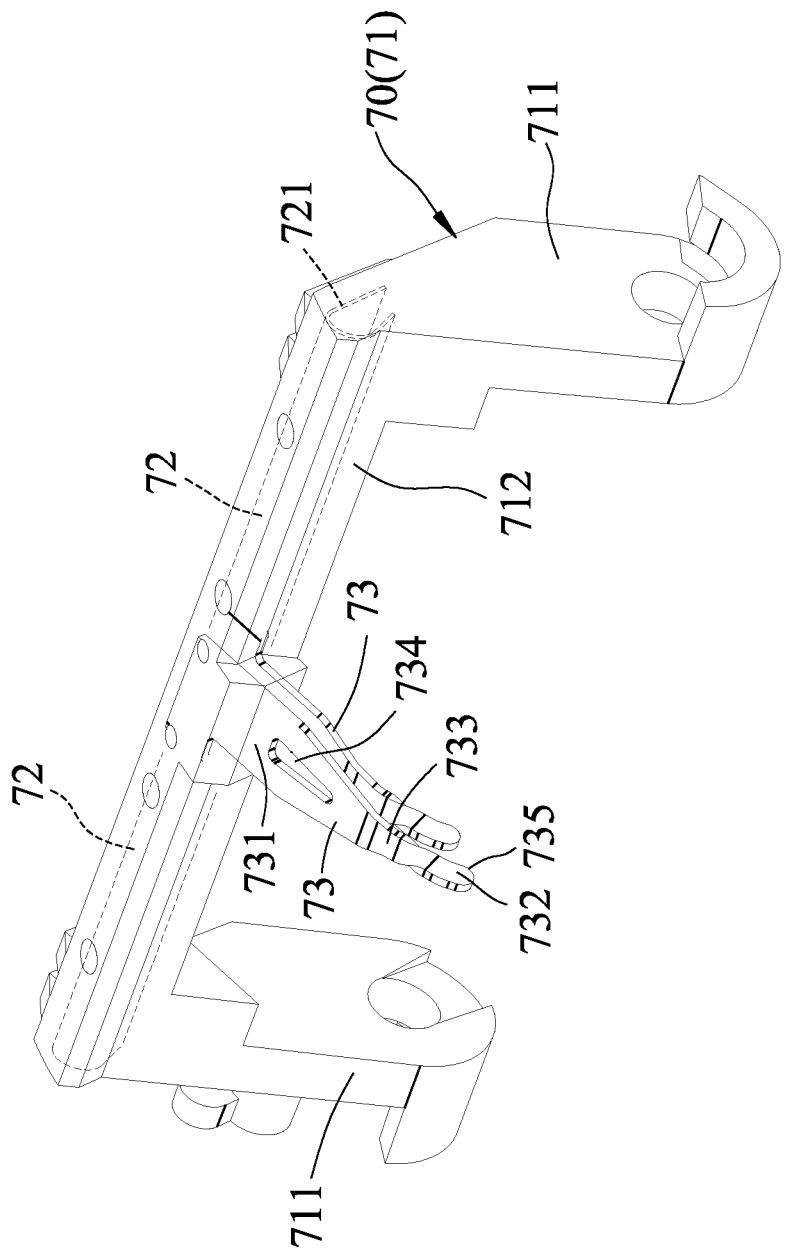
FIG. 5 is a fragmentary perspective view of a contact module of the first embodiment.
Figure 6:
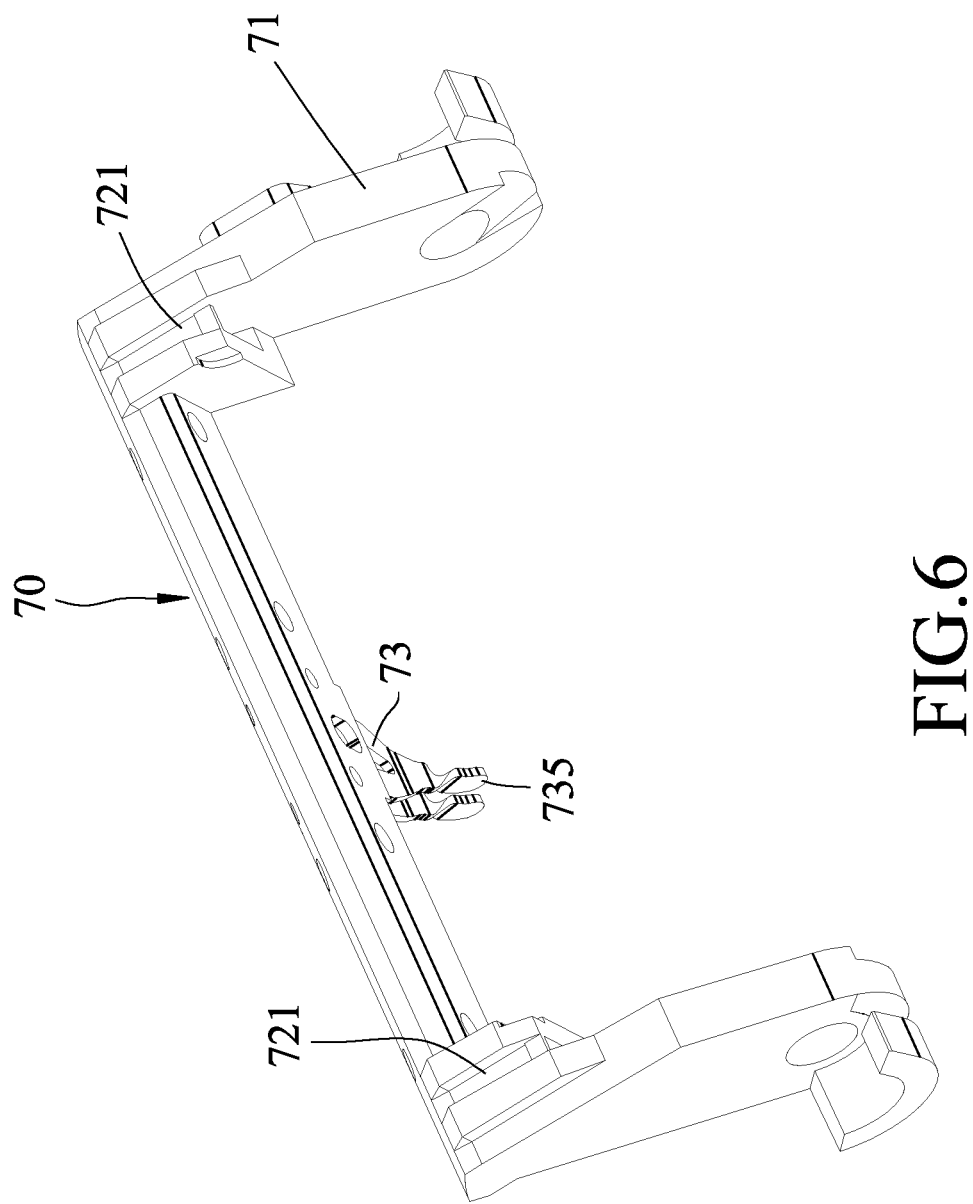
FIG. 6 is another fragmentary perspective view of the contact module.

Referring further to FIGS. 5 and 6, the contact module 70 is mounted to the base body 10, is configured to be connected electrically to the electronic module 1, and is driven pivotally by the actuating unit 60. When the actuating unit 60 is at the initial position, the contact module 70 is separated from the biosensor strip 2. When the actuating unit 60 is at the securing position, the contact module 70 is in contact with the biosensor strip 2 for electrically connecting the biosensor strip 2 to the electronic module 1.

The contact module 70 further includes a main body 71, two metallic conducting pieces 72, two extending pieces 73, two torsion springs 74 and an extension spring 75.

The main body 71 is made of an insulating material, and has two swing arms 711 pivoted respectively to the pivot poles 19 of the base body 10, and a linking rod 712 interconnecting the swing arms 711. The metallic conducting pieces 72 are embedded in the linking rod 712 of the main body 71, are electrically conductive, and are spaced apart from each other. Each of the metallic conducting pieces 72 has a contact portion 721 projecting out of the linking rod 712 of the main body 71. The extending pieces 73 are electrically and respectively connected to the metallic conducting pieces 72 and extend out of the main body 71. Each of the extending piece 73 has a base portion 731 connected to the respective one of the metallic conducting pieces 72 and formed with a slot 734, an extending portion 732 configured to be in contact with the biosensor strip 2 and has a sliding end 735, and a connecting portion 733 interconnecting the base portion 731 and the extending portion 732. The torsion springs 74 are disposed between the swing arms 711 and the base body 10 for biasing the main body 71 toward the biosensor strip 2 to thereby ensure contact between the contact portions 721 of the metallic conducting pieces 72 and the biosensor strip 2 when the actuating unit 60 is at the initial position. Each of the torsion springs 74 has a leg that is configured to be connected electrically to the electronic module 1, and another leg that is connected electrically to the contact portion 721 of a respective one of the metallic conducting pieces 72. The extension spring 75 is movably connected between the main body 71 and the spring hook 622 of one of the lower actuating seats 62 of the actuating unit 60.

The first driving spring 80 is connected between the rotating plate 50 and the actuating unit 60. In the present embodiment, the first driving spring 80 is a torsion spring, and has a spring body 81, and two legs 82, 83 connected respectively to opposite ends of the spring body 81 and engaging respectively the first connecting hole 56 of the rotating plate 50 and the second connecting hole 615 of the actuating unit 60.

The second driving spring 90 is connected between the first end 11 of the base body 10 and the spring hook 622 of the other one of the lower actuating seats 62 of the actuating unit 60. After the actuating unit 60 is moved from the securing position to an ejecting position (see FIG. 23), the second driving spring 90 is operable for driving the actuating unit 60 to move forwardly from the ejecting position to the initial position. In the present embodiment, the second driving spring 90 is a tension spring.

The resilient unit 100 is mounted between the base body 10 and the strip seat 20, and is configured for biasing resiliently and downwardly the strip seat 20 from the upper position toward the lower position. In the present embodiment, the resilient unit 100 includes a plurality of torsion springs 110. Each of the torsion springs 110 has a spring body 111 sleeved on the base body 10, a first leg 112 connected to an end of the spring body 111 and abutting against the base body 10, and a second leg 113 connected to another end of the spring body 111 and abutting against the strip seat 20.

For a further understanding of the functions, the technical means, and the intended effects of the collaboration of the various components of the disclosure, operational details of the first embodiment of the physiological signal monitoring device are provided as follows.

Referring again to FIG. 1, when the first embodiment of the physiological signal monitoring device is fully assembled and the biosensor strip 2 is not inserted therein, the rotating plate 50 is in the original position, and the guide seat 30 is proximate to the first end 11 of the base body 10 with the extension piece 32 thereof abutting against the abutment rib 29 of the strip seat 20. The projecting piece 611 of the actuating unit 60 abuts against the hook portion 53, such that the actuating unit 60 is positioned relative to the base body 10 and is at the initial position. Referring further to FIG. 32(a), at this time, by virtue of the configuration of the slide groove 24 of the strip seat 20, the anchoring member 40 is bent with the wedge portion 413 disposed at the limit section 243 of the slide groove 24 and above the insertion groove 23, such that the front end 231 of the insertion groove 23 is clear of obstruction and is ready for the insertion end 201 of the biosensor strip 2 to pass therethrough the position of the anchoring portion 42. Referring further to FIG. 31(a), at this time, the trapezoid pieces 251 of the strip seat 20 are lifted by the lower driving members 631 such that the strip seat 20 is at the upper position, and the sliding end 735 of each of the extending pieces 73 of the contact module 70 is at a retracted position.

Figure 7:
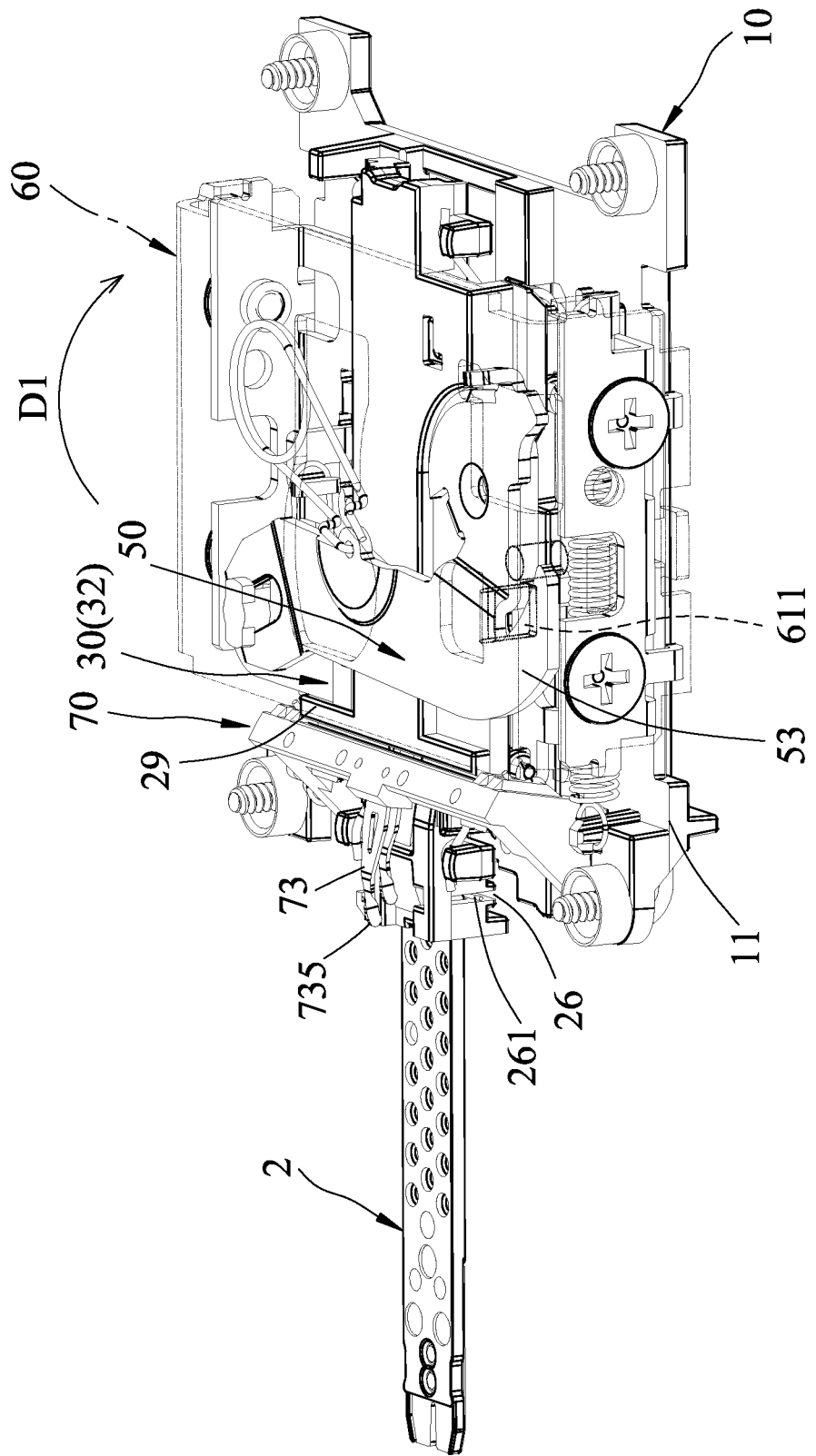
FIG. 7 is a perspective view illustrating a state of the first embodiment during an insertion process of a biosensor strip.
Figure 8:
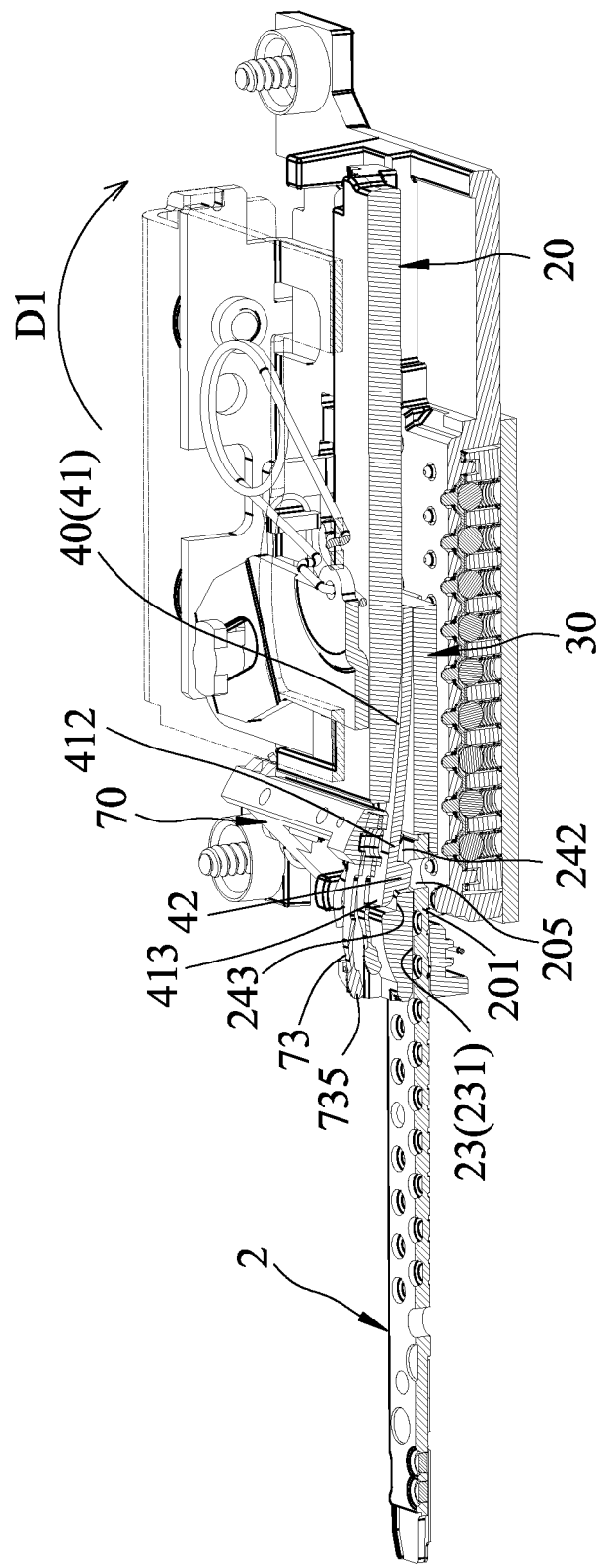
FIG. 8 is a partially cutaway perspective view of the first embodiment shown in FIG. 7.
Figure 9:
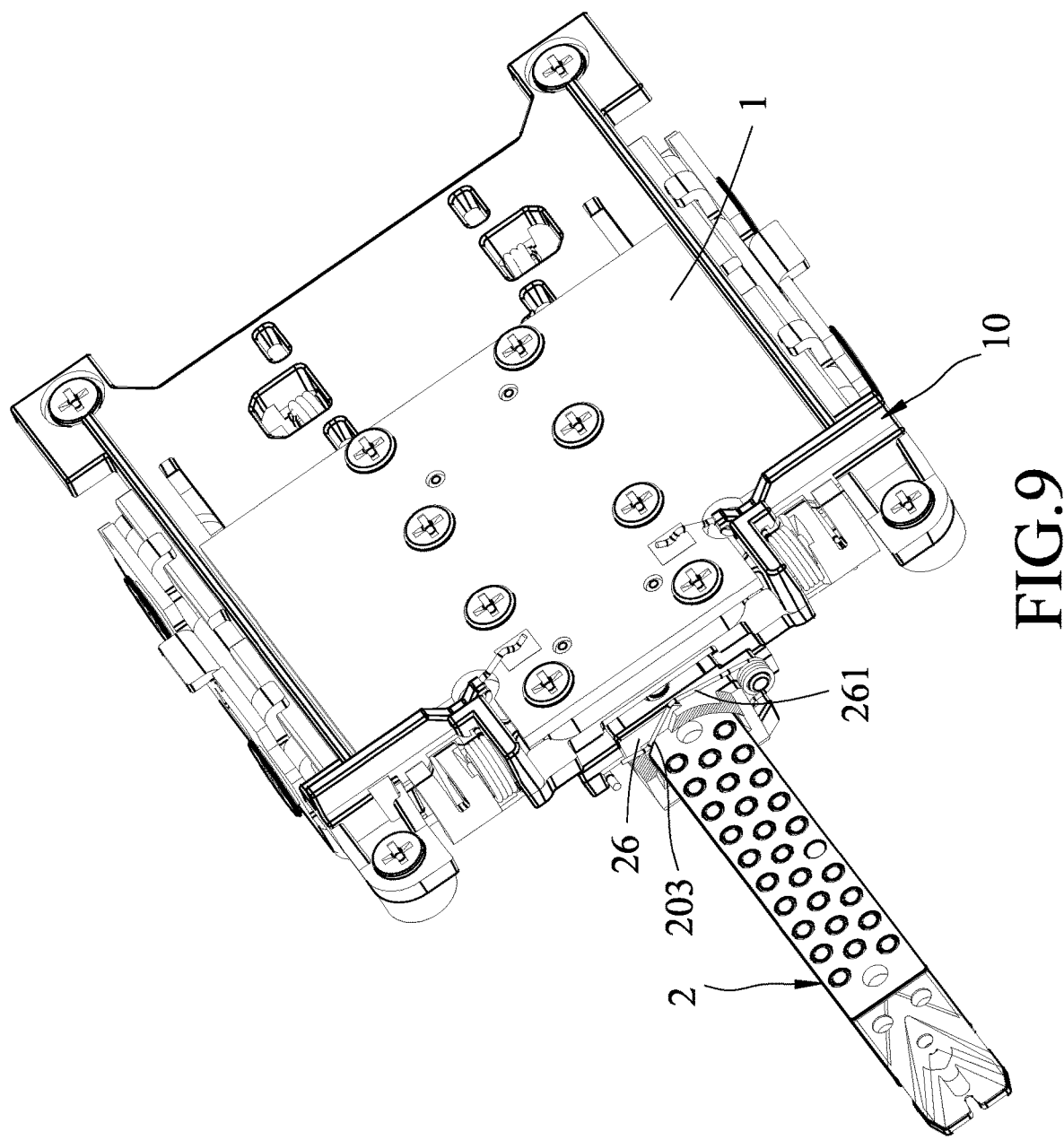
FIG. 9 is another partially cutaway perspective view of the first embodiment shown in FIG. 7.

Referring to FIGS. 7 and 8, when a user inserts the biosensor strip 2 into the physiological signal monitoring device, the insertion end 201 of the biosensor strip 2 first enters the front end 231 of the insertion groove 23 of the strip seat 20. The fool-proof edge 203 of the biosensor strip 2 is then brought into contact with the fool-proof spring 261 and pushes the fool-proof spring 261 into the fool-proof groove 26 (see FIG. 9), allowing the insertion of the biosensor strip 2 to continue. If the biosensor strip 2 is inserted in the wrong orientation (i.e., the fool-proof edge 203 does not contact the fool-proof spring 261), it will be blocked by the fool-proof spring 261 and the insertion cannot continue.

Figure 10:
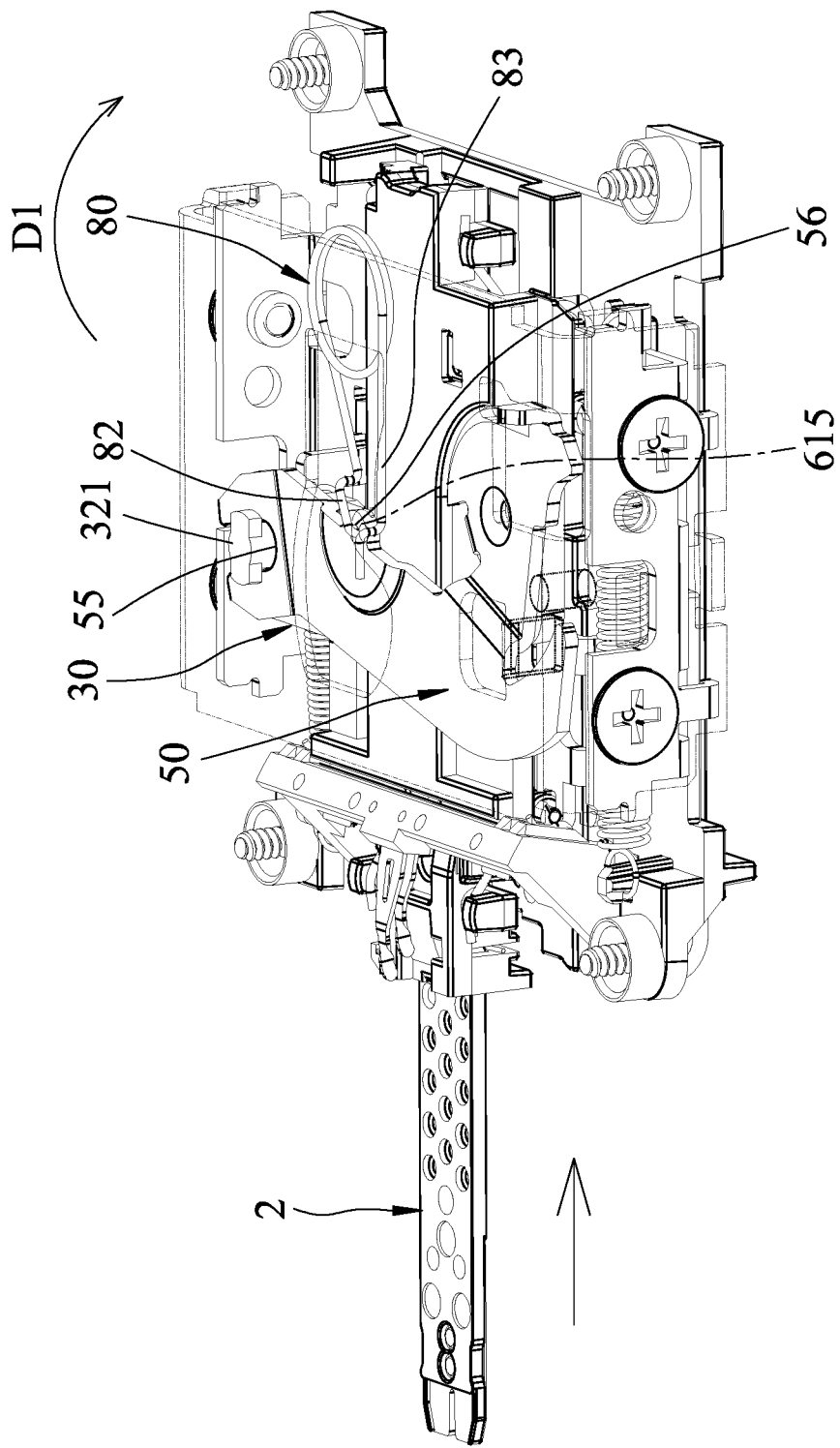
FIG. 10 is a perspective view illustrating another state of the first embodiment during the insertion process of the biosensor strip.
Figure 11:
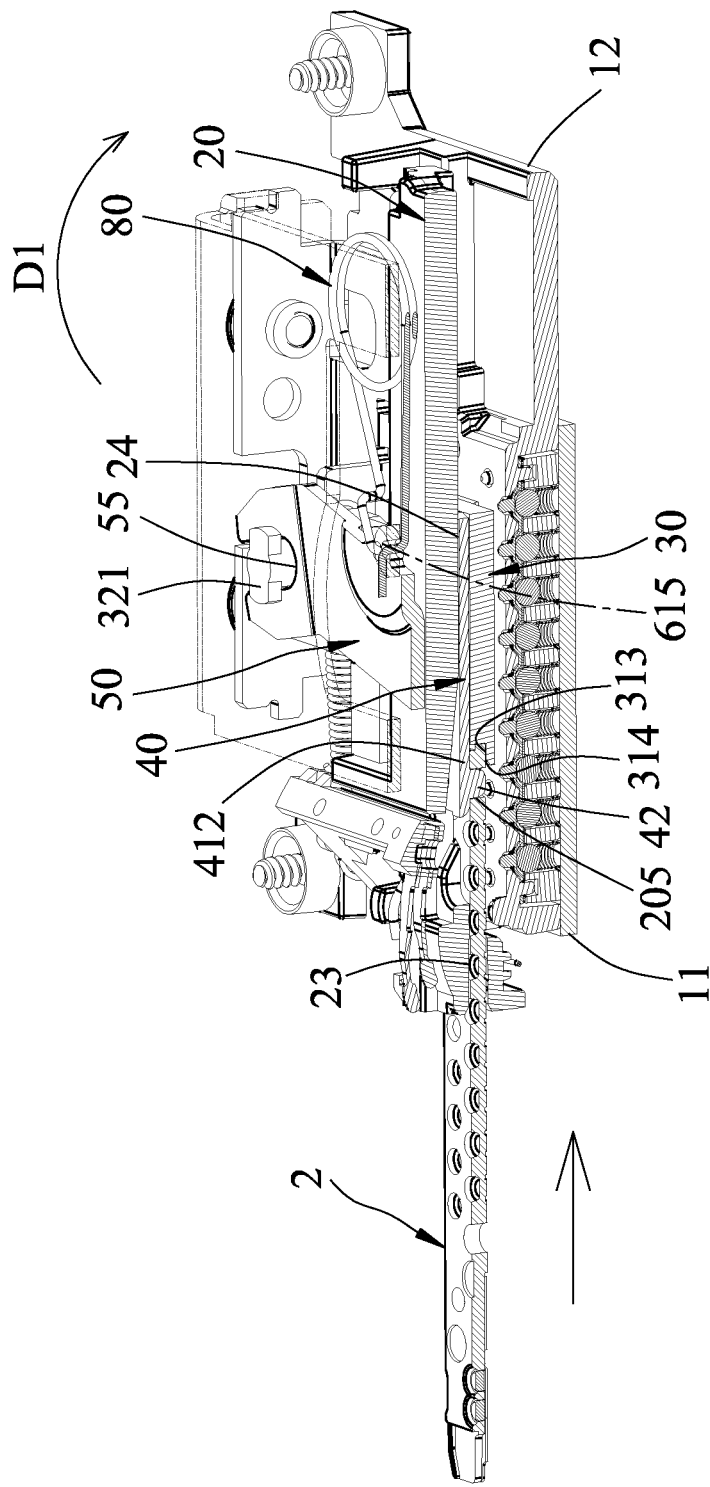
FIG. 11 is a partly cutaway perspective view of the first embodiment shown in FIG. 10.

Referring to FIGS. 10 and 11, as the user continues to push the biosensor strip 2 into the insertion groove 23 till approximately ¼ of the biosensor strip 2 (i.e., ¼ of its total length) is in the insertion groove 23, the insertion end 201 slides smoothly onto the carrying platform 313 under guidance of the inclined guide face 314 of the guide seat 30 and abuts against the guide seat 30. As the insertion of the biosensor strip 2 continues, the insertion end 201 of the biosensor strip 2 pushes the guide seat 30 to move rearwardly along an axis which extends in the front-rear direction (X) to further move the anchoring member 40 rearwardly therewith, and the wedge portion 413 of the anchoring member 40, under the guidance of the wedge section 242 of slide groove 24 of the strip seat 20, descends into the insertion groove 23 (i.e., the swingable end 412 swings downwards and the claw portion 41 of the anchoring member 40 is straightened). The anchoring portion 42 then engages with the positioning hole 207 of the biosensor strip 2 such that the biosensor strip 2 is secured between the anchoring member 40 and the guide seat 30, as shown in FIG. 32(b).

While the guide seat 30 moves rearwardly toward the second end 12, the guide seat 30 drives the rotating plate 50 to rotate in the first rotational direction (D1) via the engagement between the first coupling portion 321 and the second coupling portion 55, and further drives the first driving spring 80 to rotate in the first rotational direction (D1).

Referring to FIGS. 10 and 11, when the insertion continuous till approximately ⅓ of the biosensor strip 2 (i.e., ⅓ of its total length) is in the insertion groove 23, the rotation of the rotating plate 50 actuates an operation of the first driving spring 80 to drive the rotating plate 50 to rotate further in the first rotational direction (D1), and to push the guide seat 30 and the anchoring member 40 to move rearwardly further for further drawing the biosensor strip 2 rearwardly.

Figure 12:
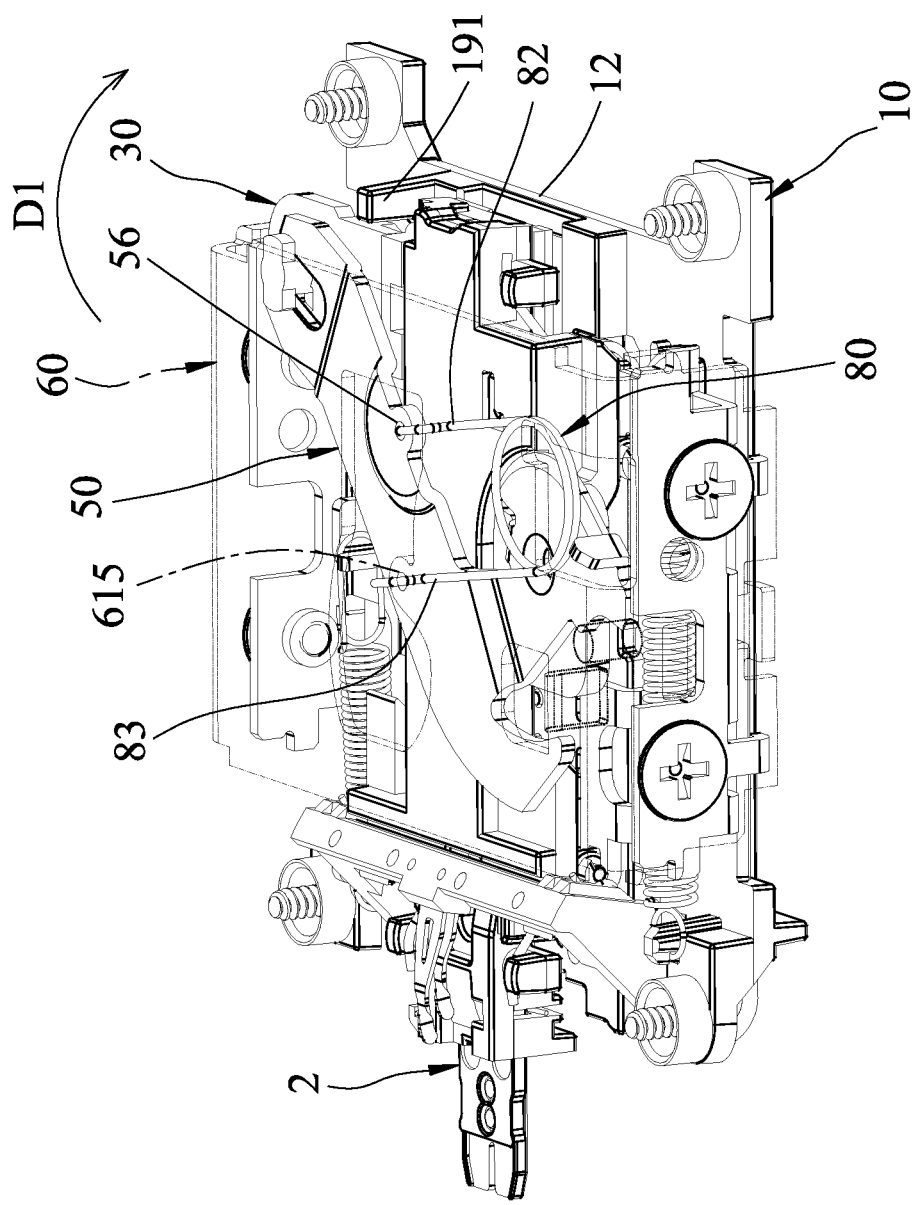
FIG. 12 is a perspective view illustrating yet another state of the first embodiment during the insertion process of the biosensor strip.
Figure 13:
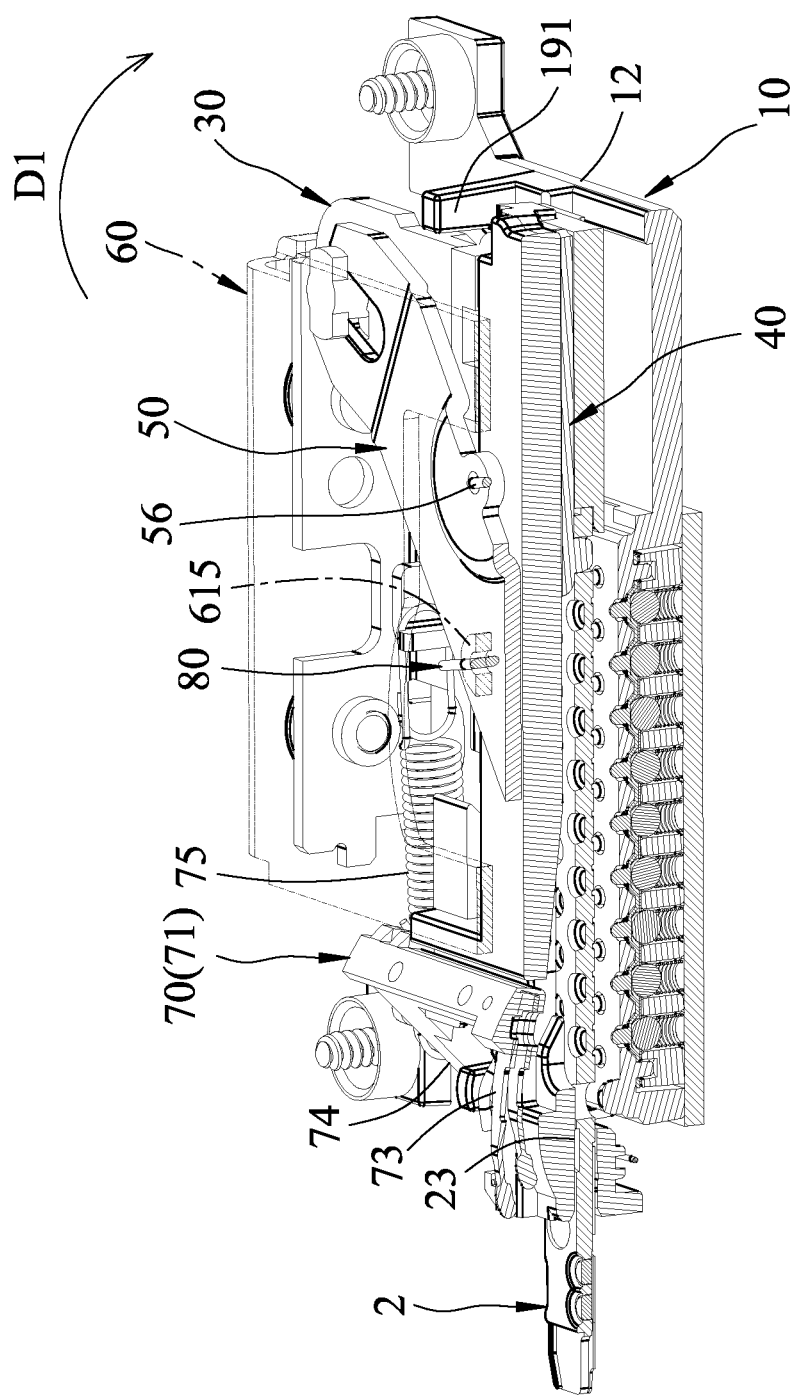
FIG. 13 is a partially cutaway perspective view of the first embodiment shown in FIG. 12.
Figure 33:
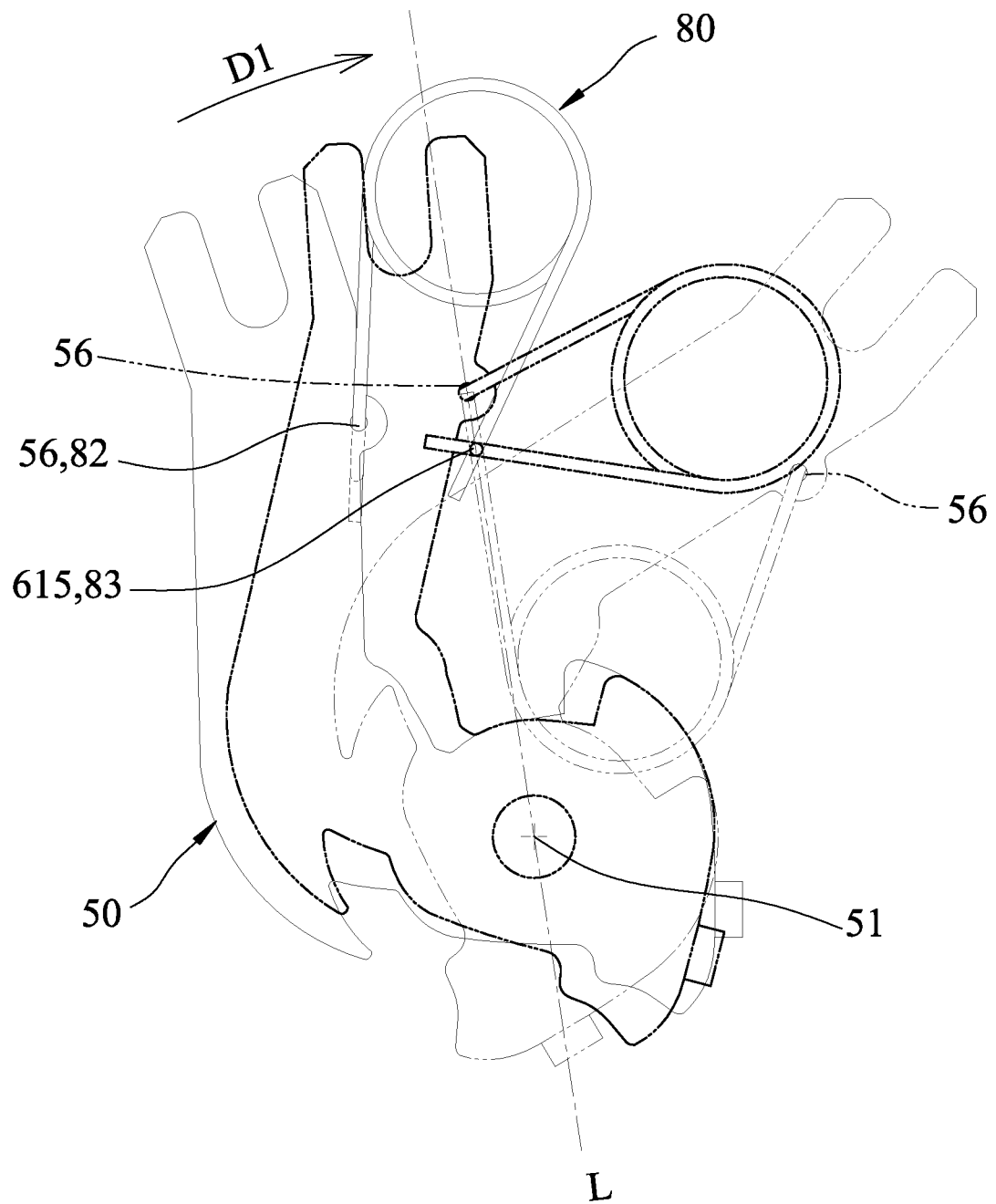
FIG. 33 is a top view illustrating rotations of a rotating plate and a first driving spring of the first embodiment.

Specifically, during the rotation of the rotating plate 50, the first connecting hole 56 becomes aligned with an imaginary straight line (L) (see FIG. 33) defined by the second connecting hole 615 and the rotational center of the rotating plate 50 (i.e., the engaging member 51), at this time, a distance between the first connecting hole 56 and the second connecting hole 615 reaches a minimum, and a distance between the leg 82 and leg 83 of the first driving spring 80 also reaches a minimum (the first driving spring 80 contains the greatest elastic energy during the whole operation). Referring to FIGS. 12, 13 and 33, it should be noted that, before the first connecting hole 56 becomes aligned with the imaginary straight line (L) defined by the second connecting hole 615 and the engaging member 51, the first connecting hole 56 is disposed at one side of the imaginary straight line (L) and the distance between the first connecting hole 56 and the second connecting hole 615 is decreasing, and as the insertion continues, the first connecting hole 56 moves to the other side of the imaginary straight line (L) and is no longer aligned with the second connecting hole 615 and the engaging member 51, and the distance between the first connecting hole 56 and the second connecting hole 615 begins to increase. During passing of the moment of alignment, the aforementioned movement of the first connecting hole 56 and the distance change between the first connecting hole 56 and the second connecting hole 615 result in a rebound effect where the first driving spring 80 experiences a sudden loss of compression and begins to bounce back and release its elastic energy to facilitate the movement of the first connecting hole 56 (i.e., rotation of the first connecting hole 56 about the engaging member 51). As such, after the moment of alignment, a resilience felt by the user prior to the moment of alignment disappears, and the rotation of the first connecting hole 56 can be solely driven by the biasing force of the first driving spring 80. As the first driving spring 80 continues to move in the first rotational direction (D1), the guide seat 30 and the anchoring member 40 continue to be driven by the rotating plate 50 to move toward the second end 12 of the base body 10, drawing the biosensor strip 2 further into the insertion groove 23, until the guide seat 30 is stopped by the stop pole 191 of the base body 10. That is, once the first driving spring 80 starts to bounce back after the moment of alignment, the user no longer has to exert force onto the biosensor strip 2, and the rest of the insertion process becomes automatic.

Figure 14:
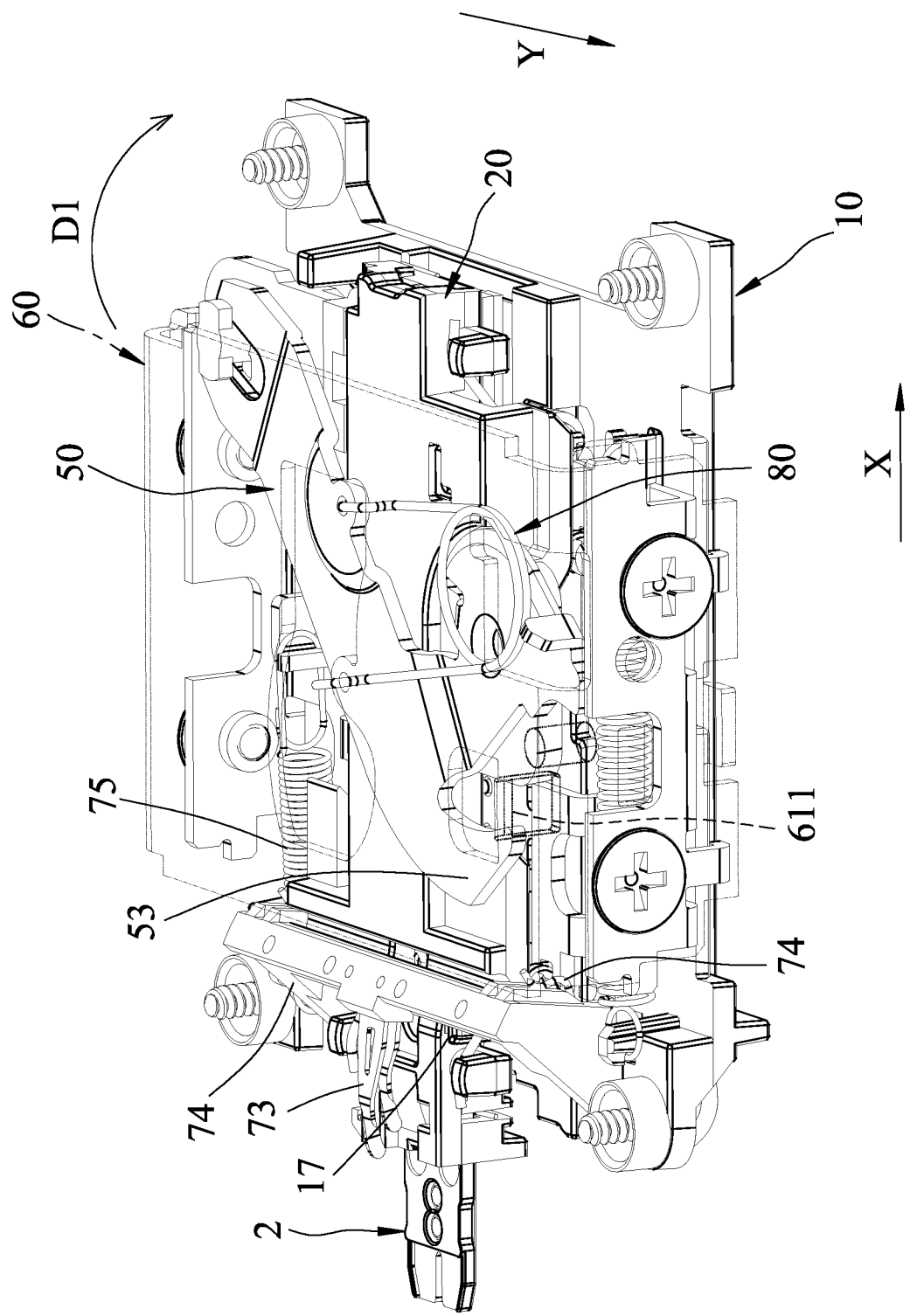
FIG. 14 is a perspective view illustrating yet another state of the first embodiment during the insertion process of the biosensor strip.
Figure 15:
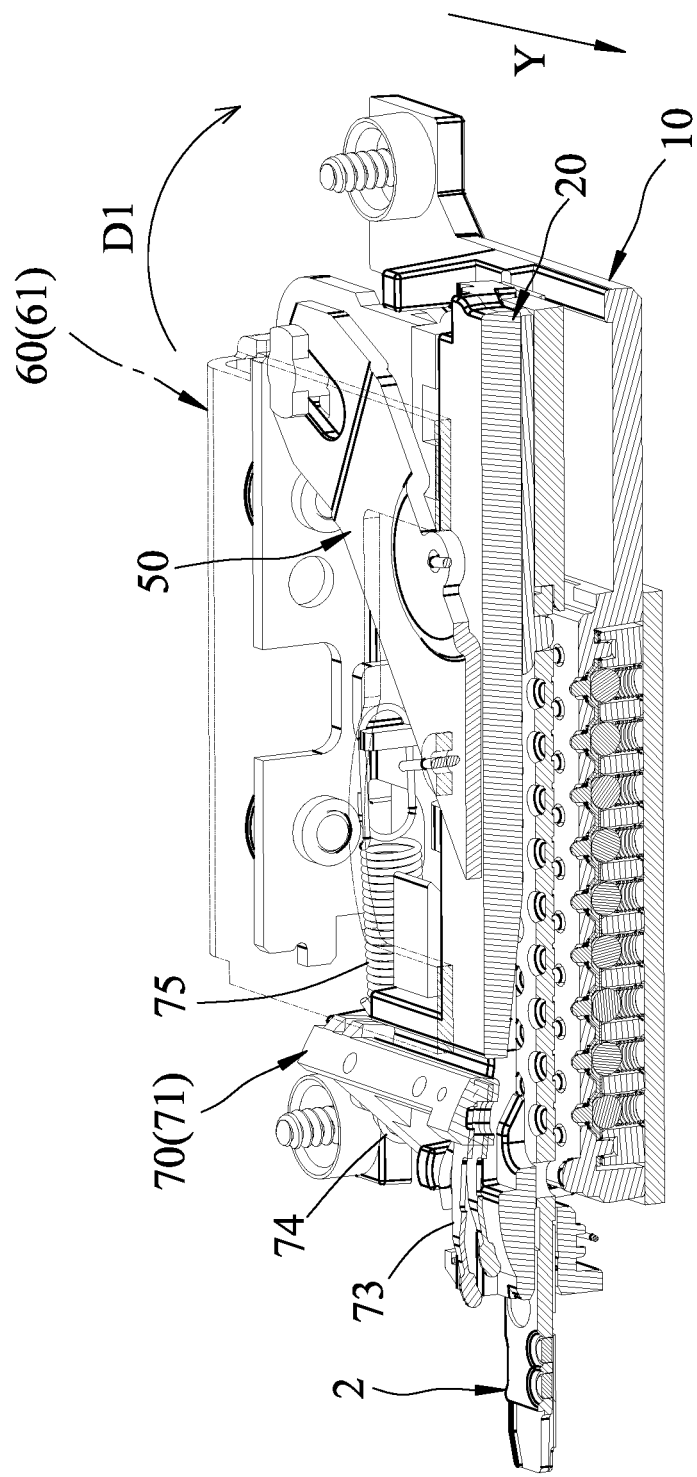
FIG. 15 is a partially cutaway perspective view of the first embodiment shown in FIG. 14.

Referring to FIGS. 14 and 15, after the insertion of the biosensor strip 2 is completed, the hook portion 53 of the rotating plate 50 is moved to a position that no longer blocks the projecting piece 611 of the actuating unit 60 such that the actuating unit 60 is allowed to be moved by a combined biasing force of the second driving spring 90 and the first driving spring 80 toward the first end 11 of the base body 10, bringing the eject button (not shown) therewith to move forwardly until the actuating unit 60 is stopped by the front stop portions 181 of the base body 10 at the securing position. By virtue of the guidance and position-limiting effect of the guide poles 17 of the base body 10, the strip seat 20 is only allowed to move upwardly and downwardly relative to the base body 10 within a certain range (see FIG. 31(b)), and following the movement of the actuating unit 60, the extension spring 75 moves toward its equilibrium position and reduces its pulling force exerted onto the main body 71 of the contact module 70. The main body 71 is then allowed to be pivoted by the biasing force of the torsion springs 74 such that the linking rod 712 of the main body 71 moves away from the abutment rib 29 of the strip seat 20. At the same time, the extending pieces 73 of the contact module 70 move toward the signal output ends 204 of the biosensor strip 2.

Figure 2:
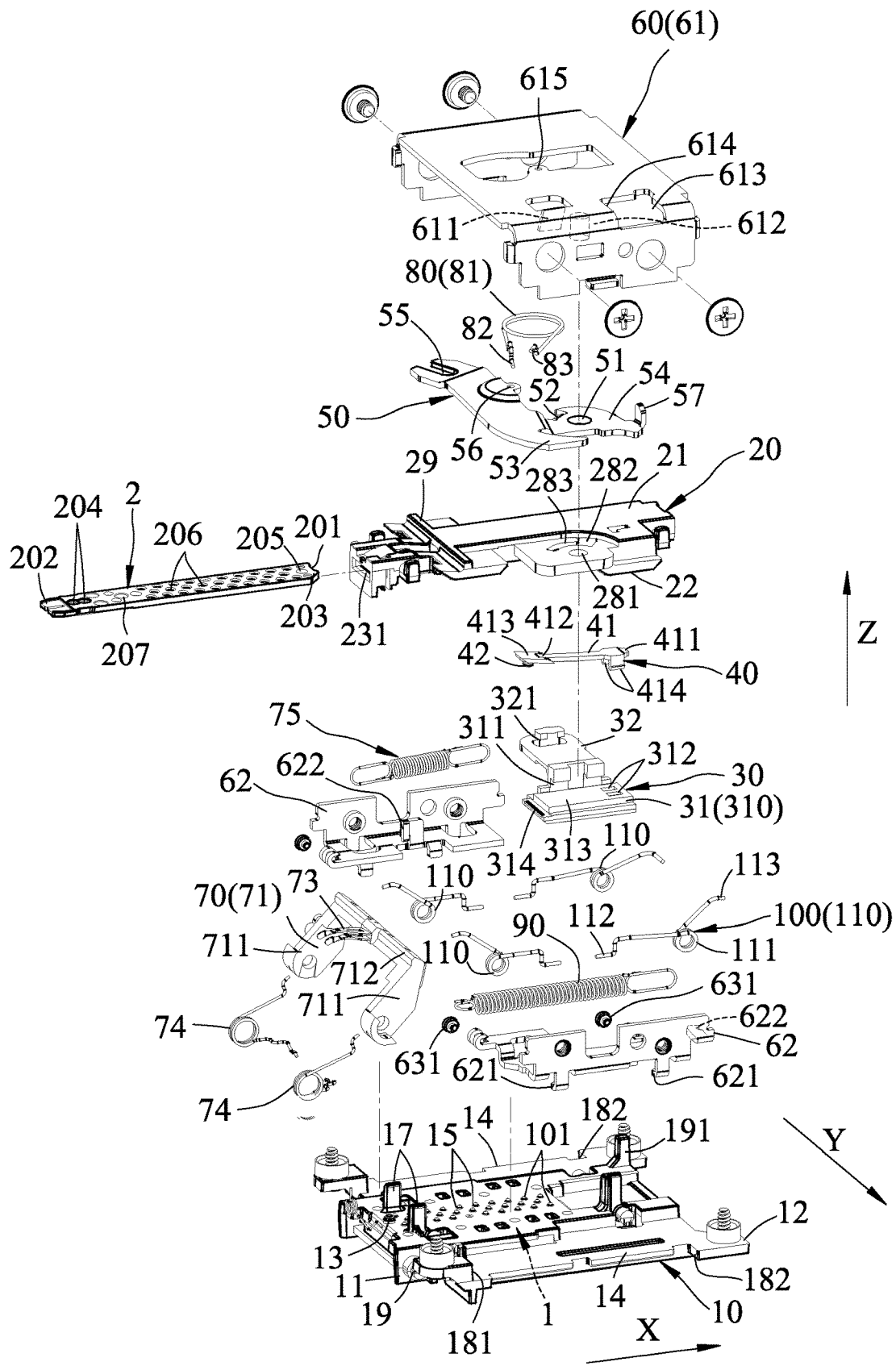
FIG. 2 is an exploded perspective view of the first embodiment.
Figure 3:
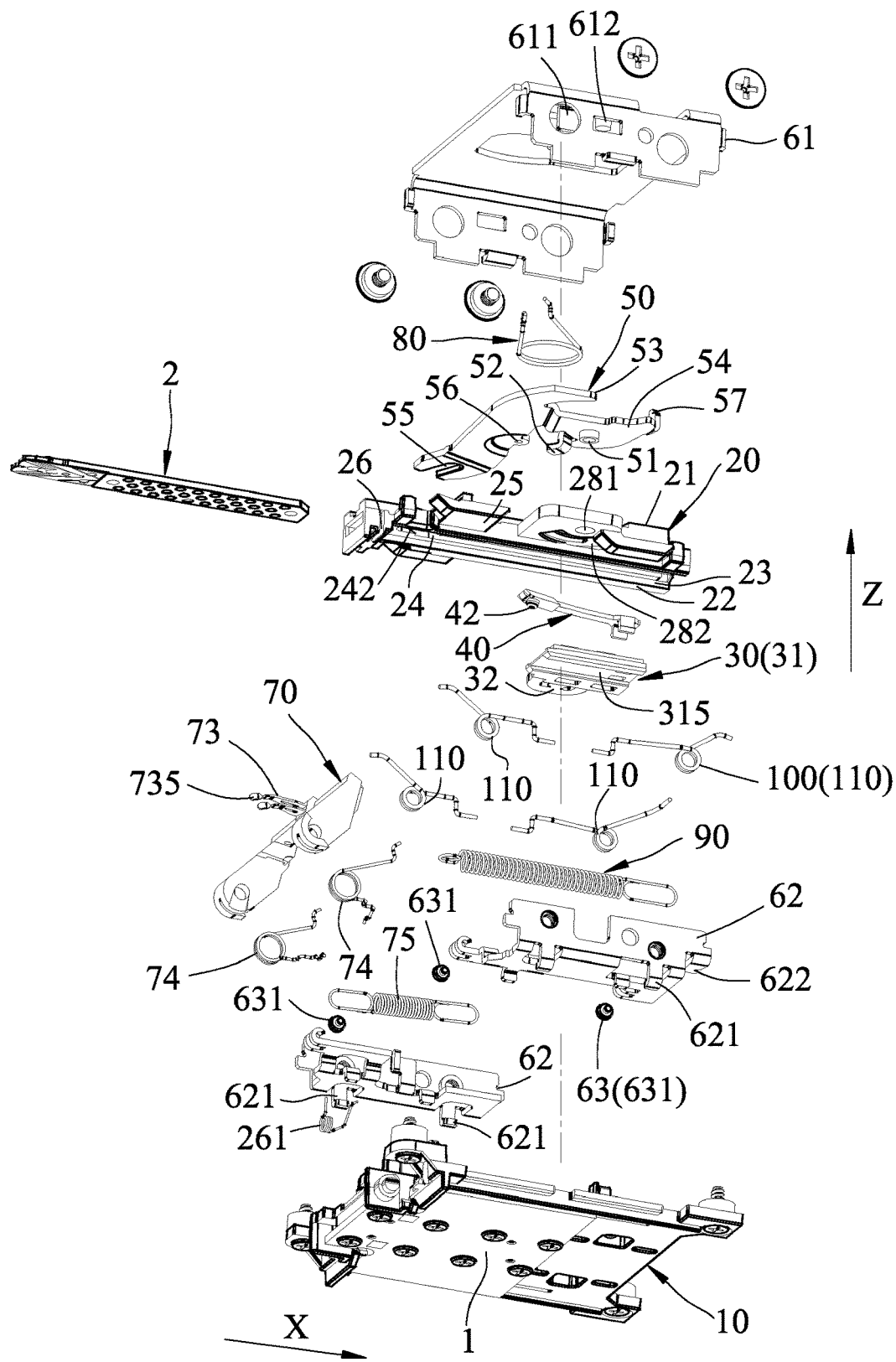
FIG. 3 is another exploded perspective view of the first embodiment.
Figure 4:
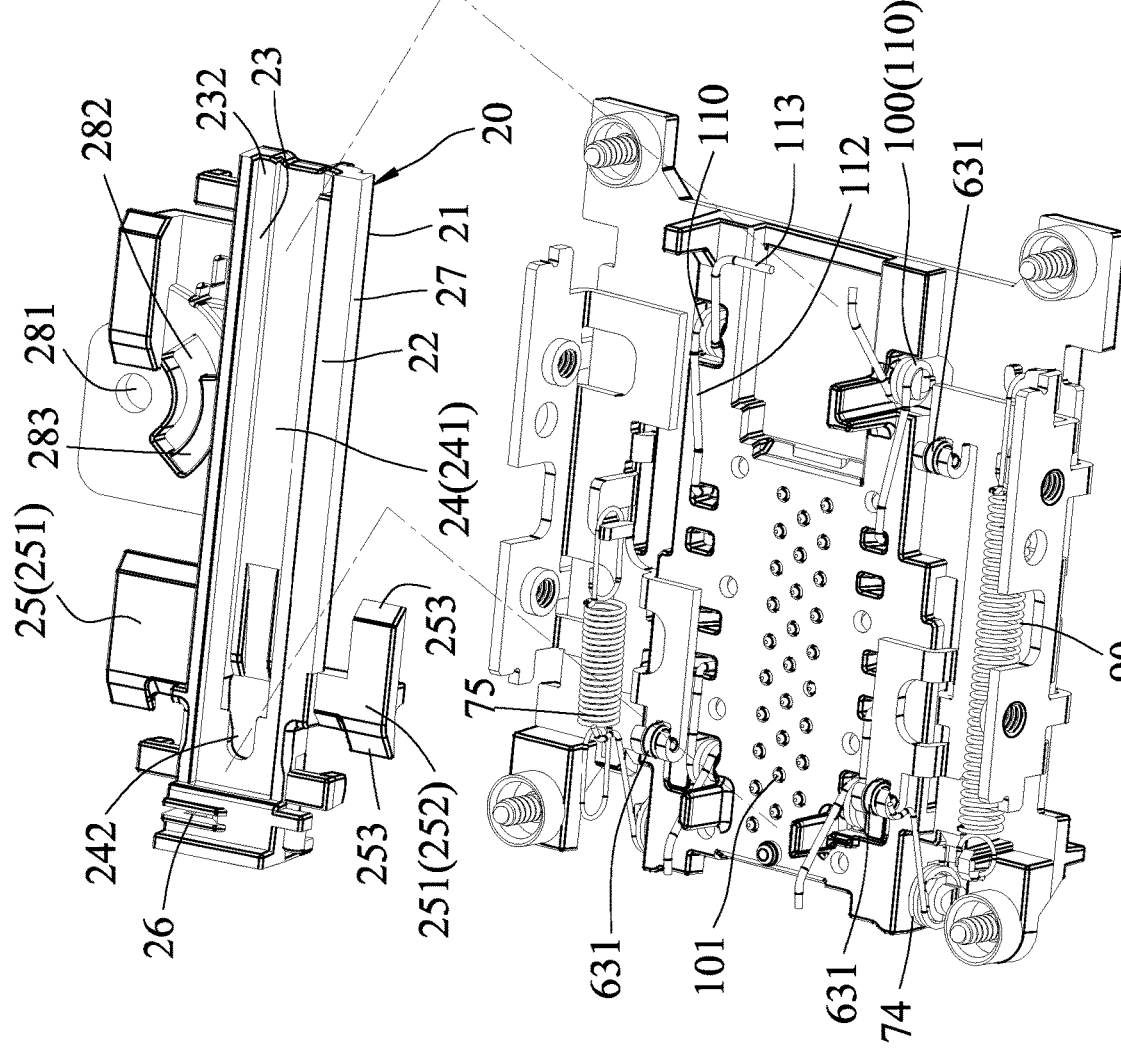
FIG. 4 is a partially exploded and fragmentary perspective view of the first embodiment, illustrating a base body, a strip seat, and two lower actuating seats.
Figure 16:
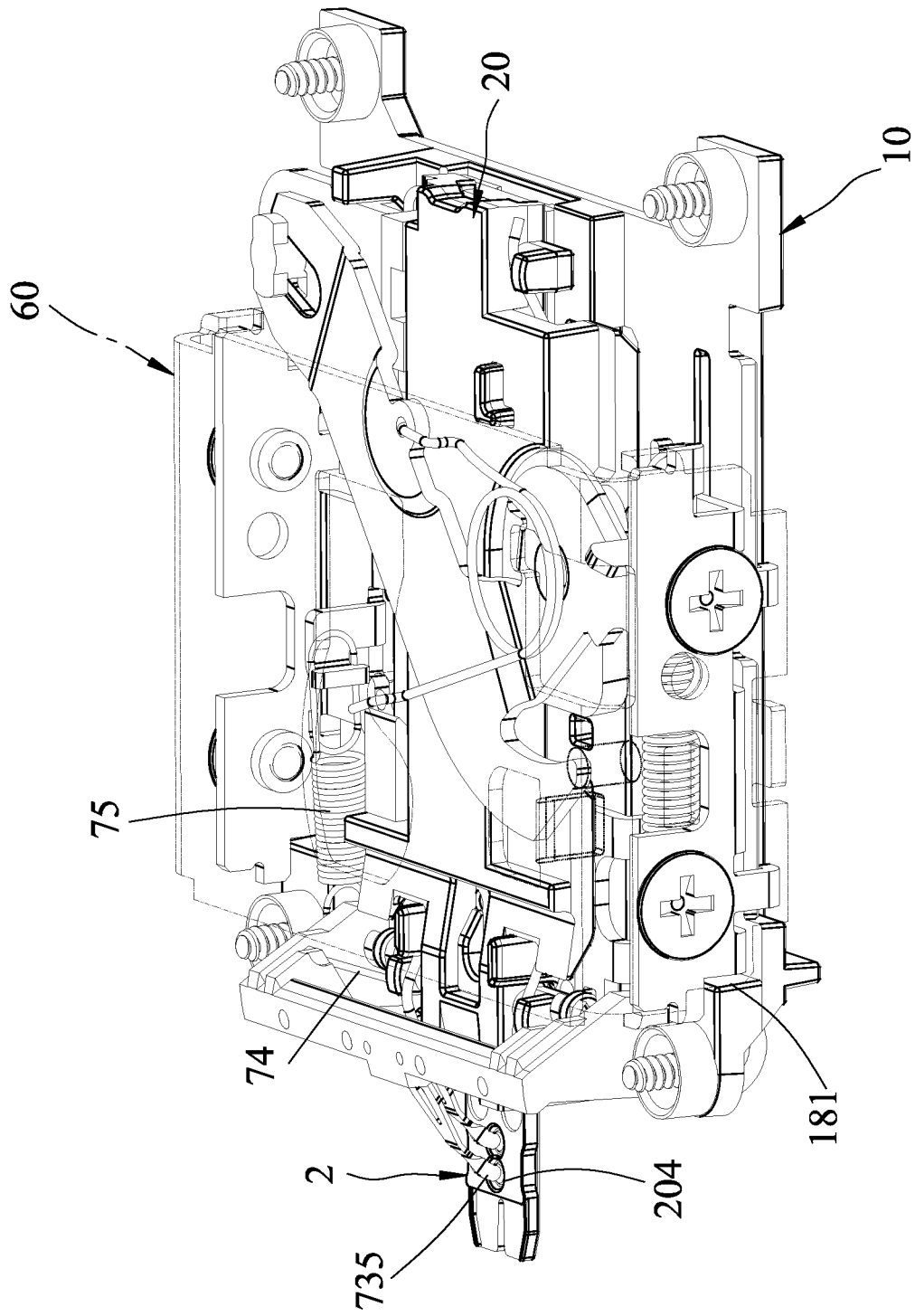
FIG. 16 is a perspective view illustrating yet another state of the first embodiment during the insertion process of the biosensor strip.
Figure 17:
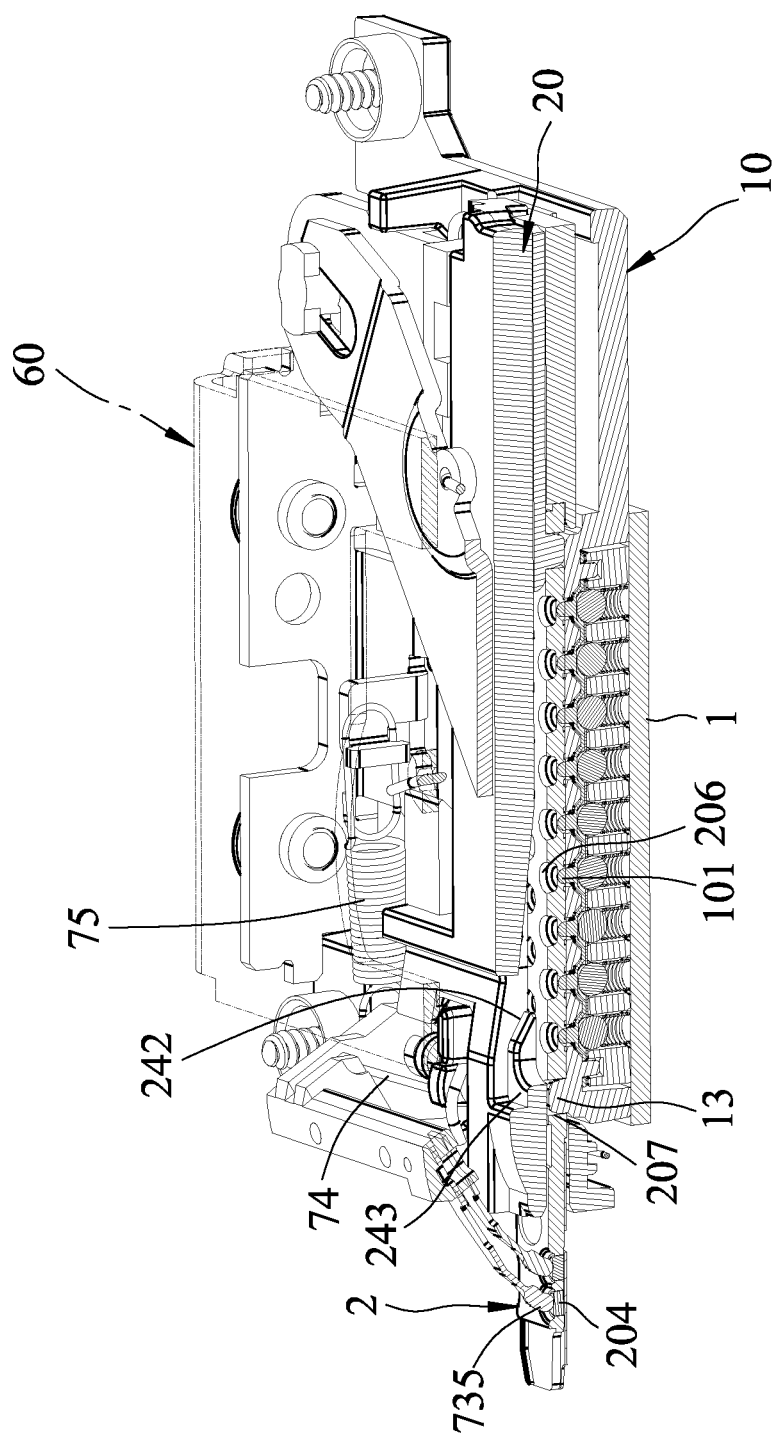
FIG. 17 is a partially cutaway perspective view of the first embodiment shown in FIG. 16.

Referring to FIGS. 16 and 17 in conjunction with FIGS. 2 and 31(b), during the movement of the actuating unit 60 toward the first end 11 of the base body 10, each of the lower driving members 631 (i.e., the rollers) of the driving set 63 rolls under the bottom surface 252 of the respective one of the trapezoid pieces 251 of the strip seat 20 toward a corresponding one of the inclined surfaces 253 until becoming separated from the respective one of the trapezoid pieces 251. When the lower driving members 631 are separated from the trapezoid pieces 251, the strip seat 20, subjected to the biasing force of the seat torsion springs 110 of the resilient unit 100, moves toward the lower position and presses the biosensor strip 2 in the insertion groove 23 against a top surface of the base body 10. As a result, the code holes 206 of the biosensor strip 2 are pressed against the code beads 101 to actuate the electronic module 1 (e.g., an automatic coding module mounted thereon), and the positioning pole 13 of the base body 10 engages the positioning hole 207 of the biosensor strip 2 such that the biosensor strip 2 is positioned with respect to the base body 10.

It should be noted that, at this time, the actuating unit 60 is not in contact with the strip seat 20 (components thereof are spaced apart by small gaps), such that the actuating unit 60 is movable relative to the base body 10 without being affected by the strip seat 20. At the same time, the extension spring 75 of the contact module 70 reaches its equilibrium position, and rotation of the main body 71 brings the sliding end 735 of each of the extending pieces 73 into contact with a respective one of the signal output ends 204 of the biosensor strip 2. By virtue of the resilience of the extending pieces 73 and the biasing force of the torsion springs 74, the sliding end 735 of each of the extending pieces 73 slides slightly on the respective one of the signal output ends 204 while making contact therewith, and generates friction that scrapes away any potential oxide layer, passivation layer or foreign objects that might interfere with the contact, thereby ensuring electrical conduction between the extending pieces 73 and the signal output ends 204. At this point, the insertion of the biosensor strip 2 is completed, and the biosensor strip 2 is electrically connected to the electronic module 1, such that the electronic module 1 is actuated to transmit physiological signals (values of current) to obtain corresponding blood glucose values.

Figure 18:
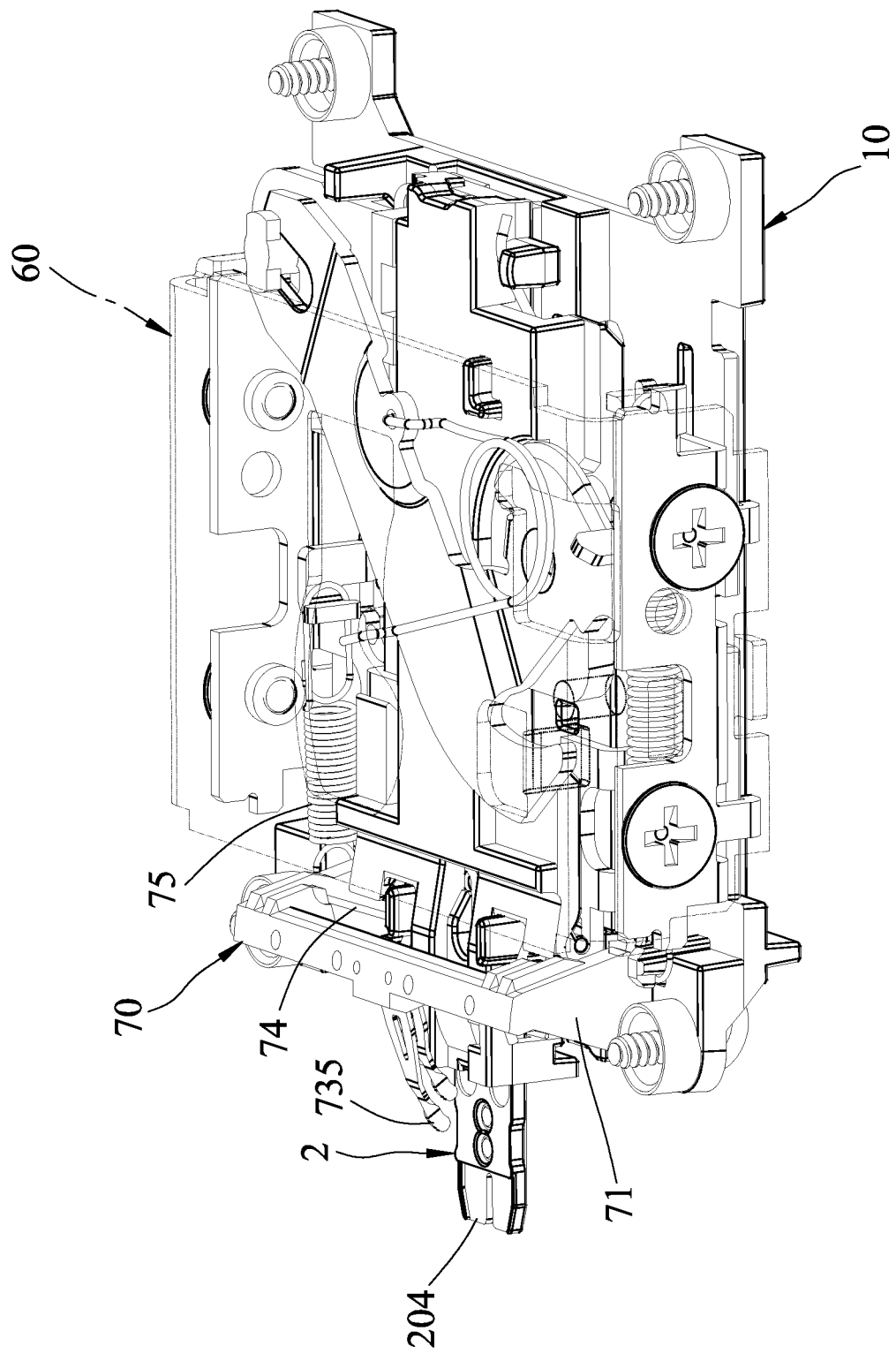
FIG. 18 is a perspective view illustrating a state of the first embodiment during an ejection process of the biosensor strip.
Figure 19:
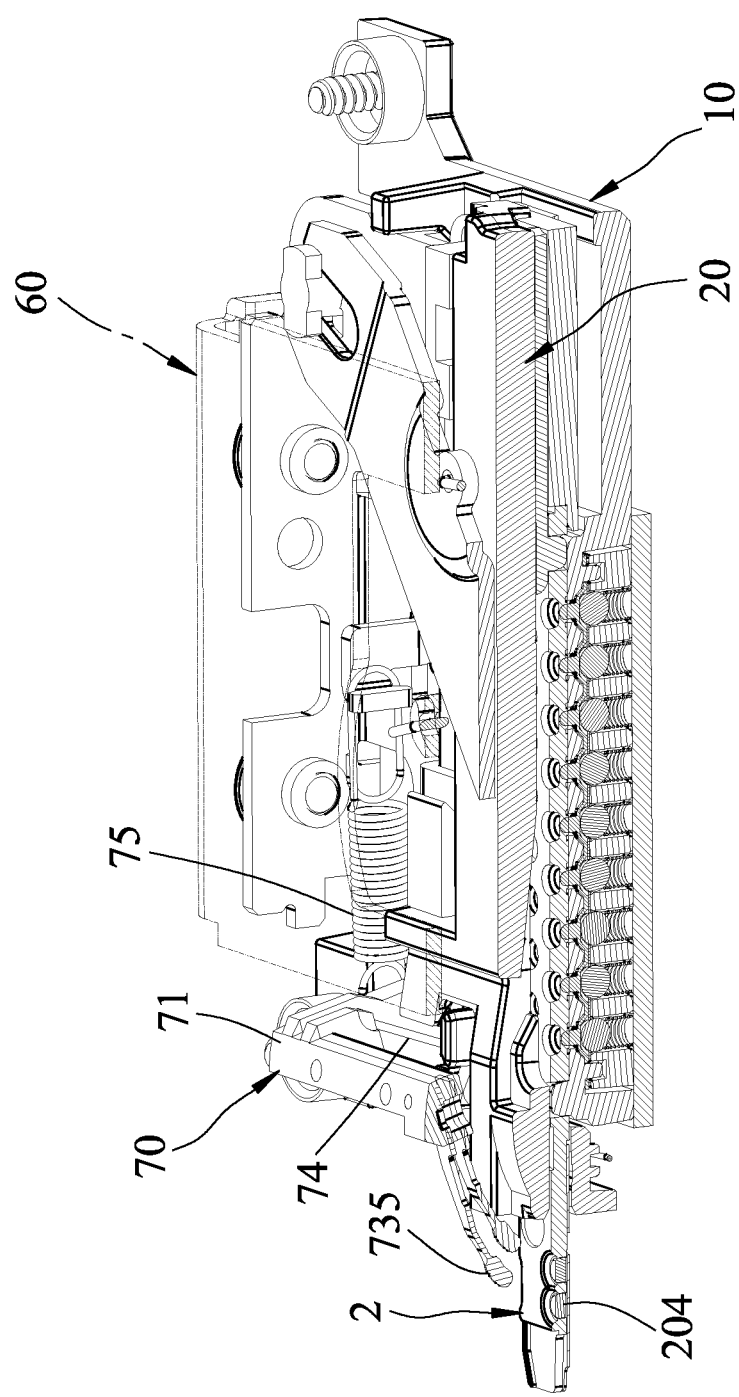
FIG. 19 is a partially cutaway perspective view of the first embodiment shown in FIG. 18.

Referring to FIGS. 18 and 19, when the user ejects the biosensor strip 2, the eject button (not shown) is pushed along the front-rear direction (X), driving the actuating unit 60 to move toward the second end 12 of the base body 10 and pull the extension spring 75 away from its equilibrium position. When the biasing force of the extension spring 75 begins to overpower the biasing force of the torsion springs 74, the main body 71 of the contact module 70 starts to pivot backwards and pull the sliding end 735 of each of the extending pieces 73 away from the respective one of the signal output ends 204 of the biosensor strip 2. During the same time, each of the lower driving members 631 of the actuating unit 60 is brought into contact with a corresponding one of the inclined surfaces 253 of the respective one of the trapezoid pieces 251 of the strip seat 20 and rolls toward the bottom surface 252 of the respective one of the trapezoid pieces 251, such that the strip seat 20 is lifted by the lower driving members 631 toward the upper position (see FIG. 31(c) and FIG. 31(d)).

Figure 20:
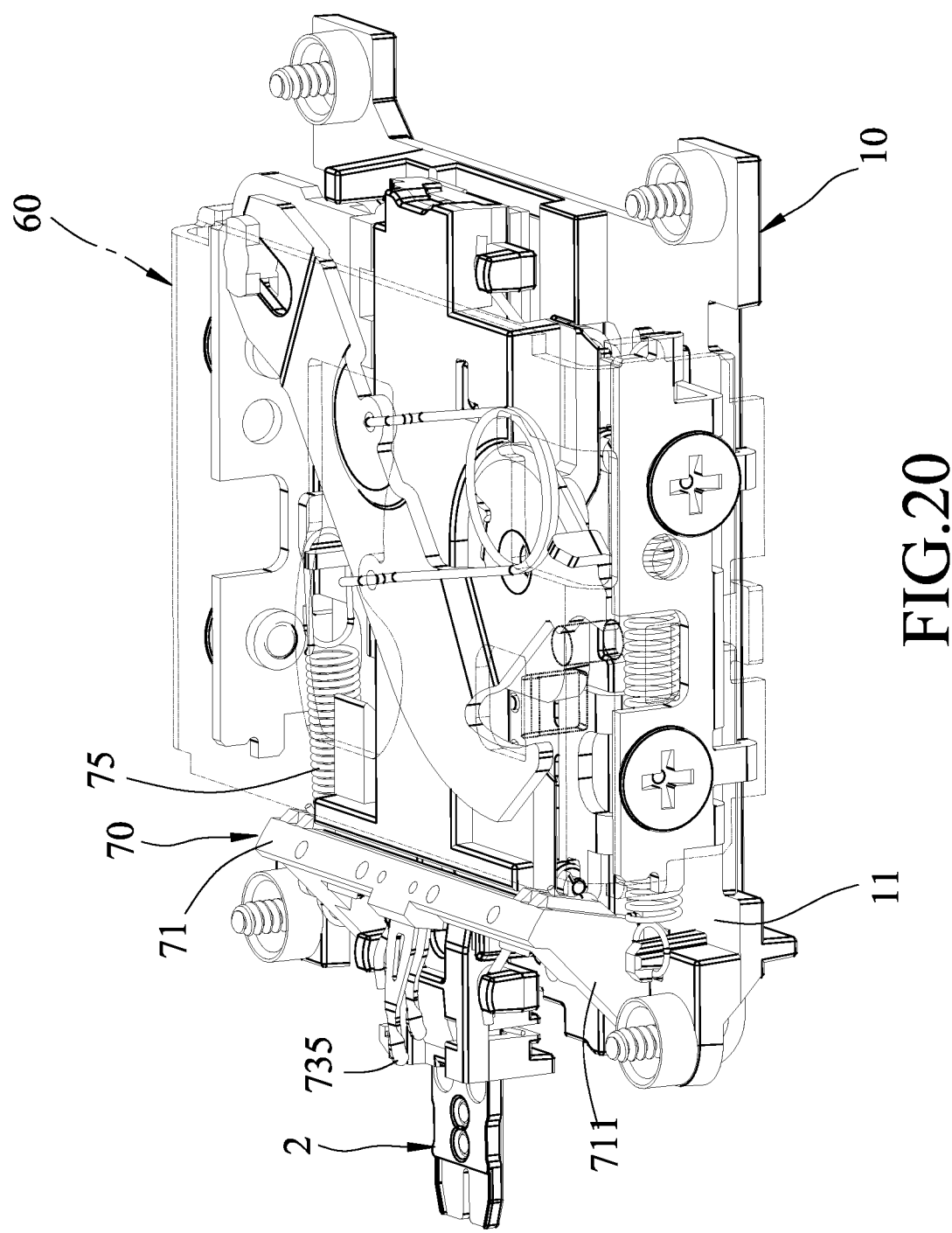
FIG. 20 is a perspective view illustrating another state of the first embodiment during the ejection process of the biosensor strip.
Figure 21:
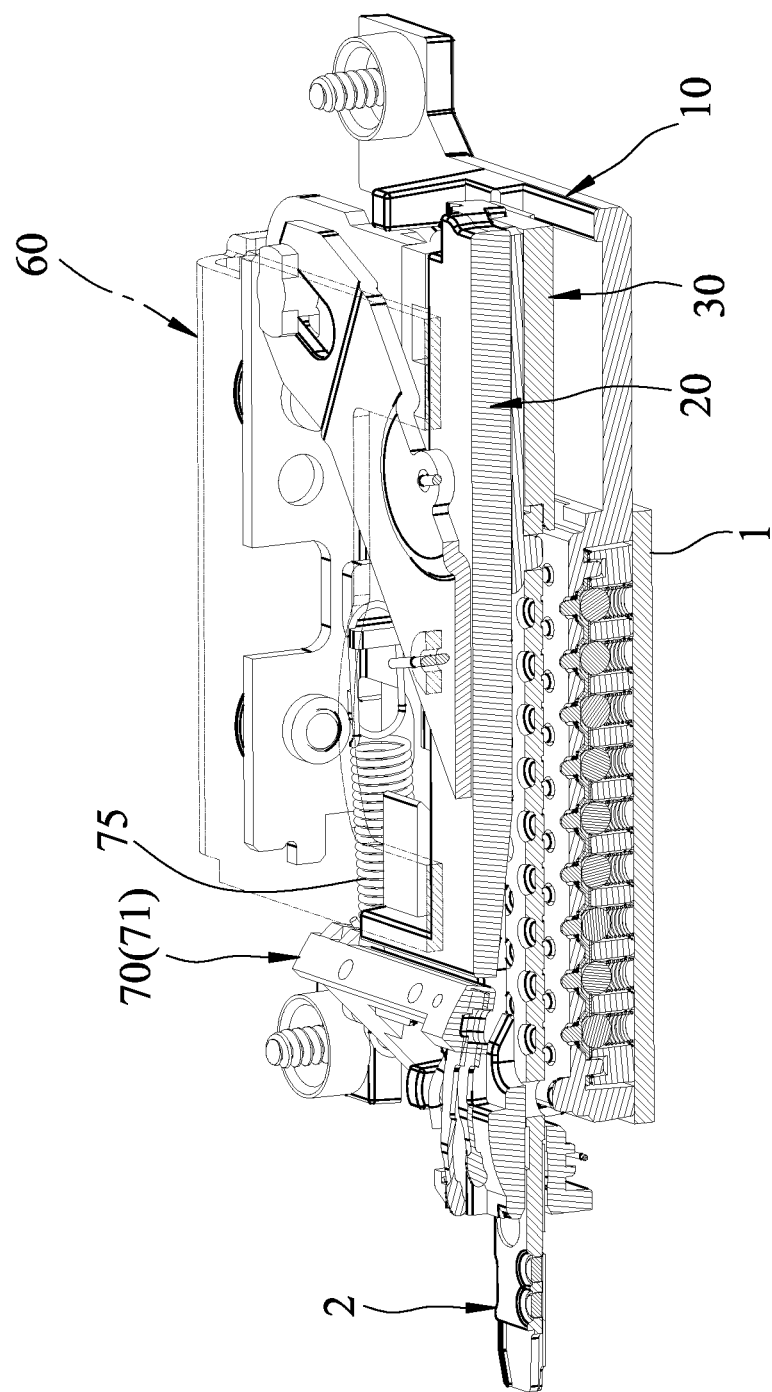
FIG. 21 is a partially cutaway perspective view of the first embodiment shown in FIG. 20.
Figure 22:
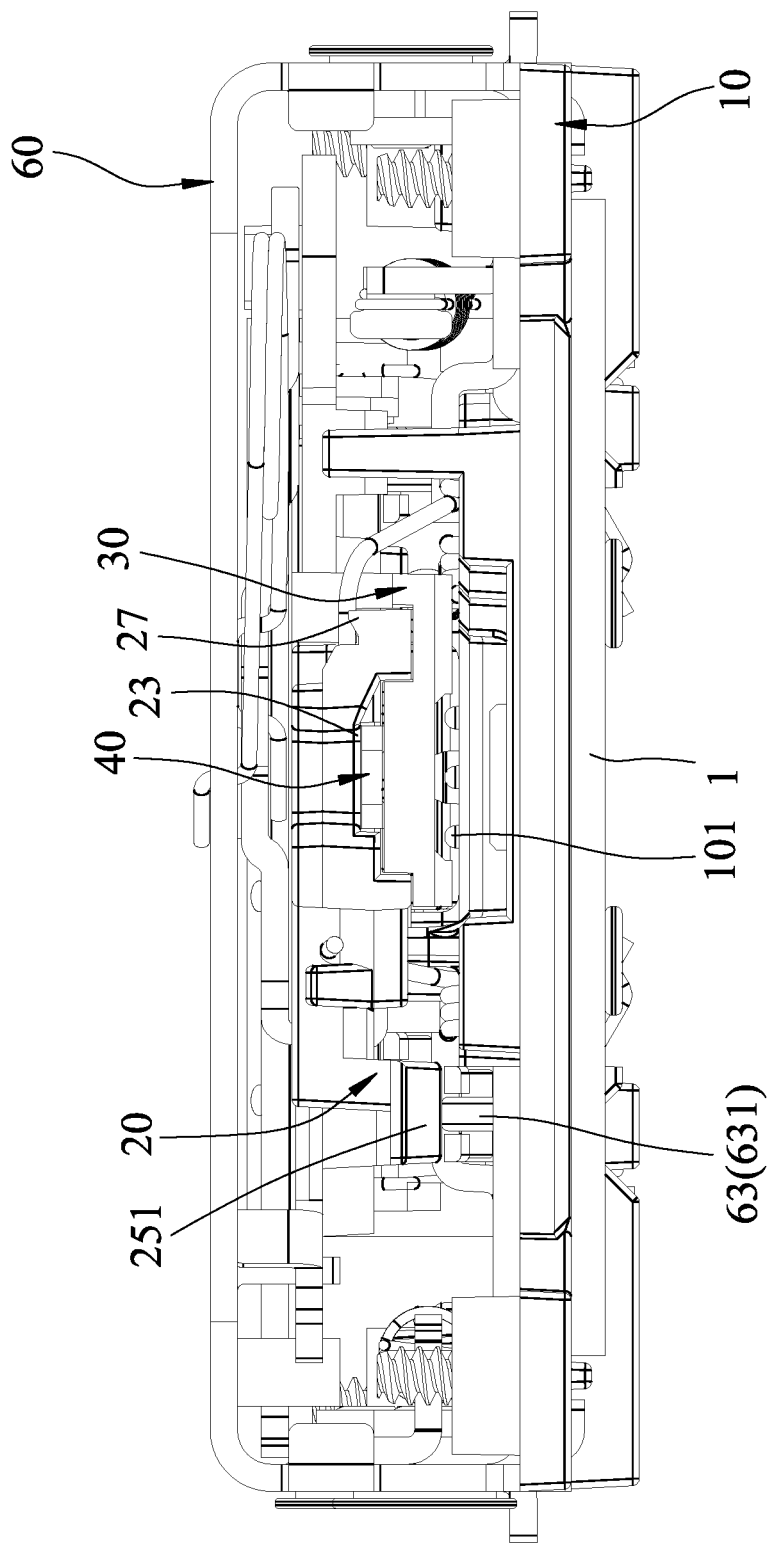
FIG. 22 is a rear view of the first embodiment shown in FIG. 20.

Referring to FIGS. 20 to 22, as the user continues to push the eject button and the actuating unit 60 continues to move toward the second end 12 of the base body 10, the extension spring 75 keeps pulling the main body 71 of contact module 70 until the swing arms 711 of the main body 71 abut against the first end 11 of the base body 10 (preventing the main body 71 from over rotation) and the sliding end 735 of each of the extending pieces 73 returns to the retracted position. At the same time, when each of the lower driving members 631 is directly under the bottom surface 252 of the respective one of the trapezoid pieces 251, the strip seat 20 is fully lifted back to the upper position (see FIG. 31(a)). Once the biosensor strip 2 is separated from the top surface of the base body 10, the electronic module 1 resets to its original state.

Figure 23:
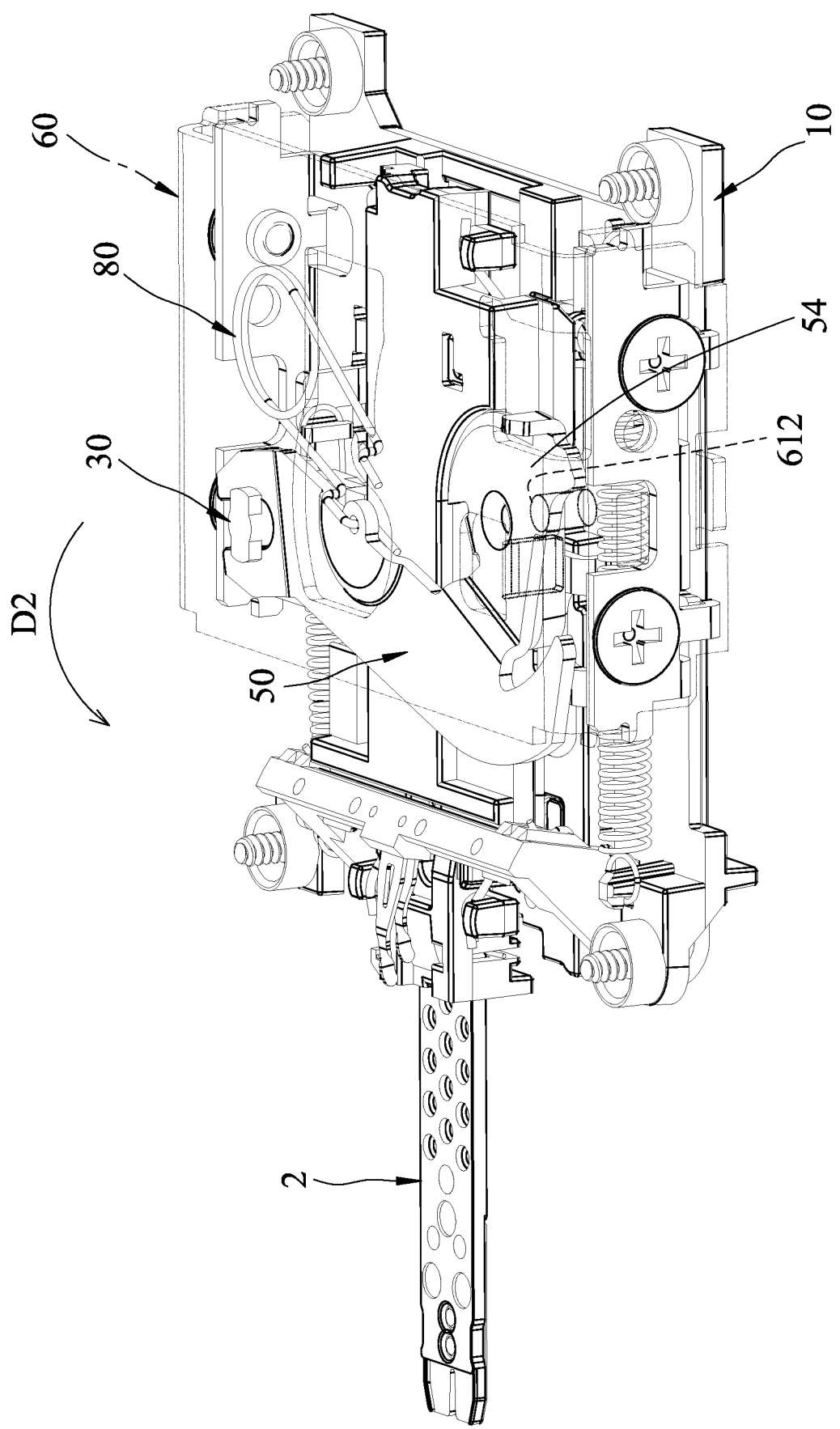
FIG. 23 is a perspective view illustrating yet another state of the first embodiment during the ejection process of the biosensor strip.
Figure 24:
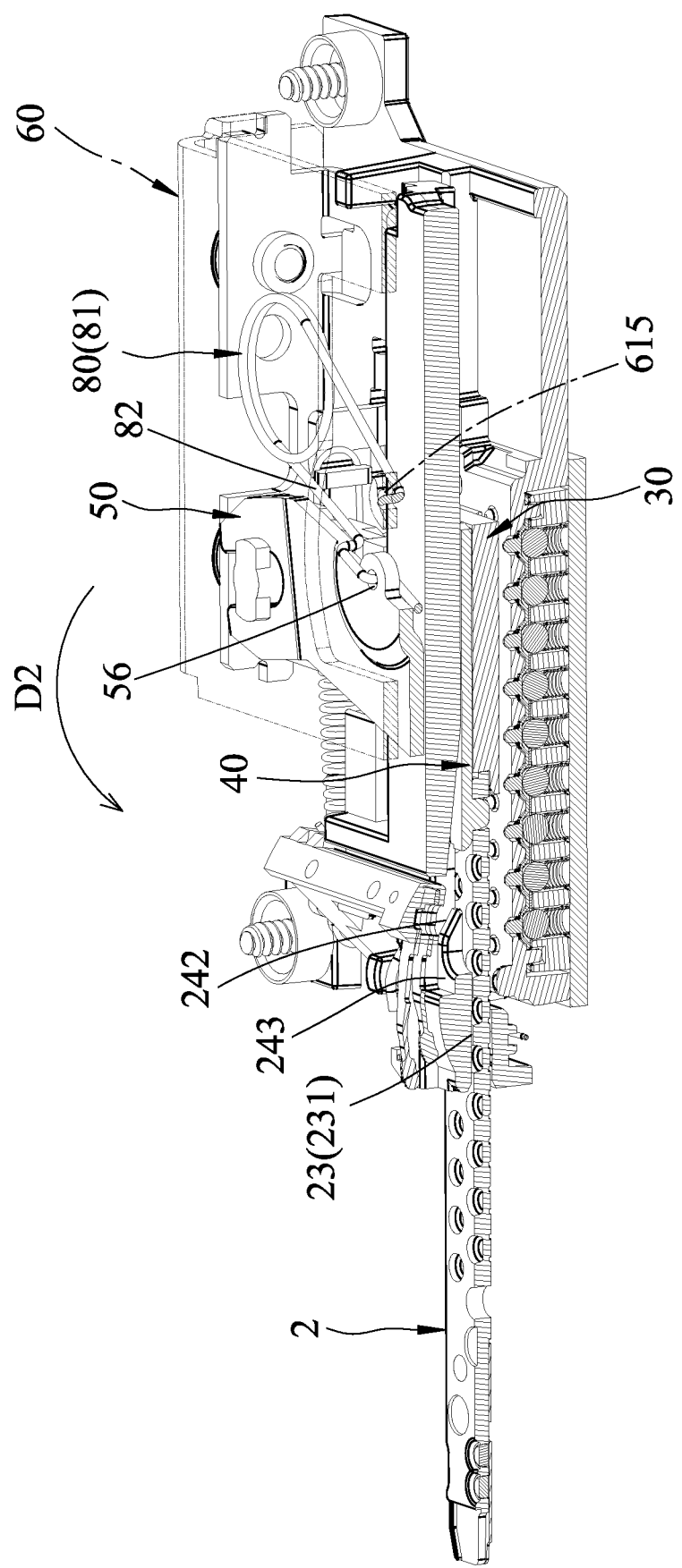
FIG. 24 is a partially cutaway perspective view of the first embodiment shown in of FIG. 23.

Referring to FIGS. 23 and 24, during movement of the actuating unit 60 toward the second end 12 of the base body 10, the projecting pin 612 of the upper actuating seat 61 abuts against and pushes the abutment portion 54 of the rotating plate 50, such that rearward movement of the actuating unit 60 drives the rotating plate 50 to rotate in a second rotational direction (D2) opposite to the first rotational direction (D1), driving the guide seat 30 and the anchoring member 40 to move forwardly and push the biosensor strip 2 out of the insertion groove 23 of the strip seat 20. During this time, the first driving spring 80 begins to rotate in the second rotational direction (D2), and the above-mentioned operation of the first driving spring 80 is actuated again to drive the rotating plate 50 to rotate further in the second rotational direction (D2), and to push the guide seat 30 and the anchoring member 40 to move forwardly further for further pushing the biosensor strip 2 forwardly. Specifically, when the first connecting hole 56, the second connecting hole 615, and the engaging member 51 are once again aligned with each other, the rebound effect of the first driving spring 80 reoccurs and the first driving spring 80 again begins to bounce back and release its elastic energy to facilitate the movements of the first connecting hole 56 and the second connecting hole 615. As such, in a similar manner as mentioned above, the rest of the ejection process of the biosensor strip 2 becomes automatic.

It should be noted that, although after the rebound effect of the first driving spring 80, the user no longer has to exert force onto the eject button to push the actuating unit 60 toward the second end 12 of the base body 10, the pushing movement of the user often continues due to the inertia thereof until the actuating unit 60 is stopped by the rear stop portions 182 of the base body 10 at the ejecting position. That is, the user does not have to push the eject button all the way to complete the ejection process.

Figure 25:
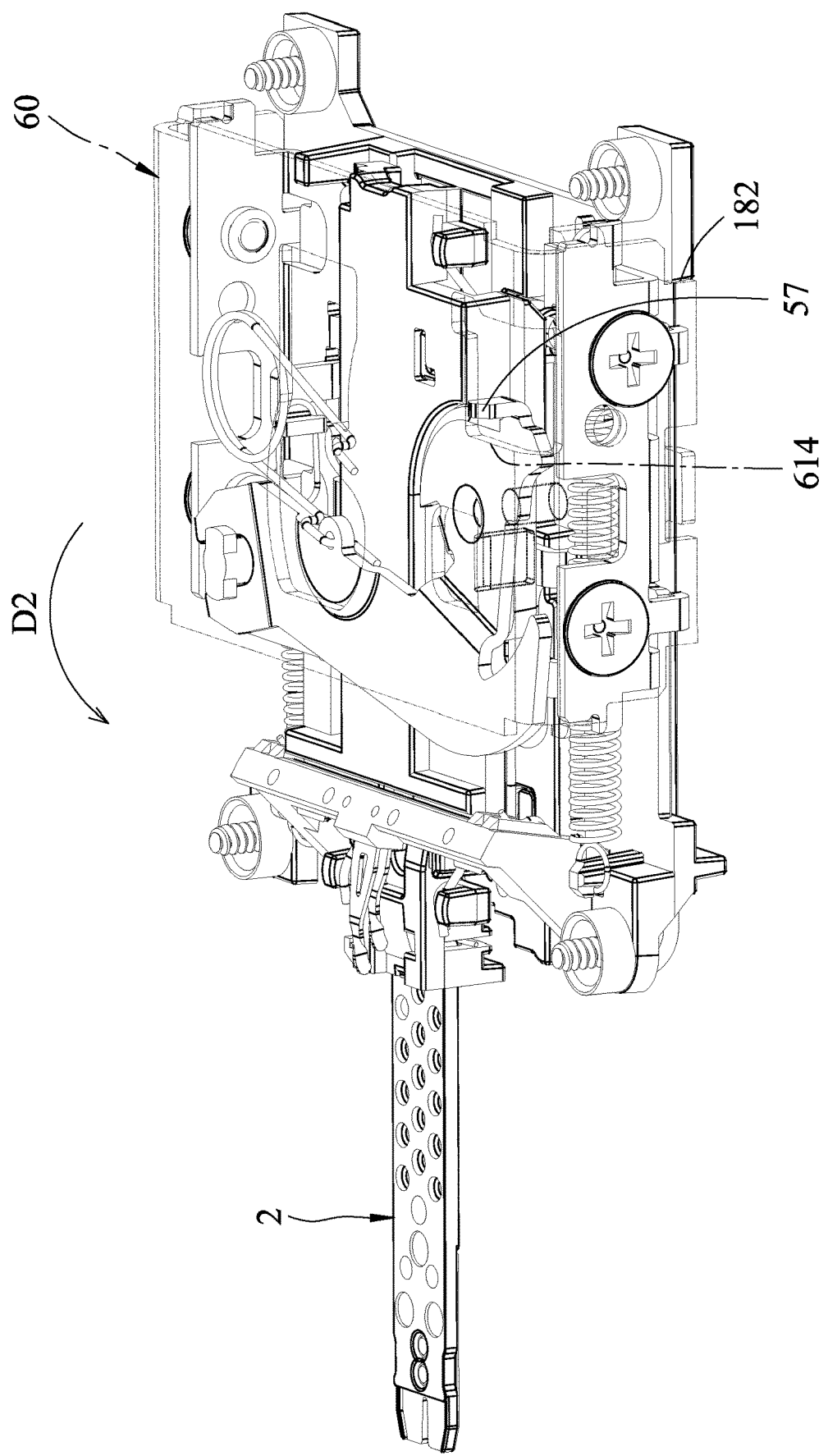
FIG. 25 is a perspective view illustrating yet another state of the first embodiment during the ejection process of the biosensor strip.
Figure 26:
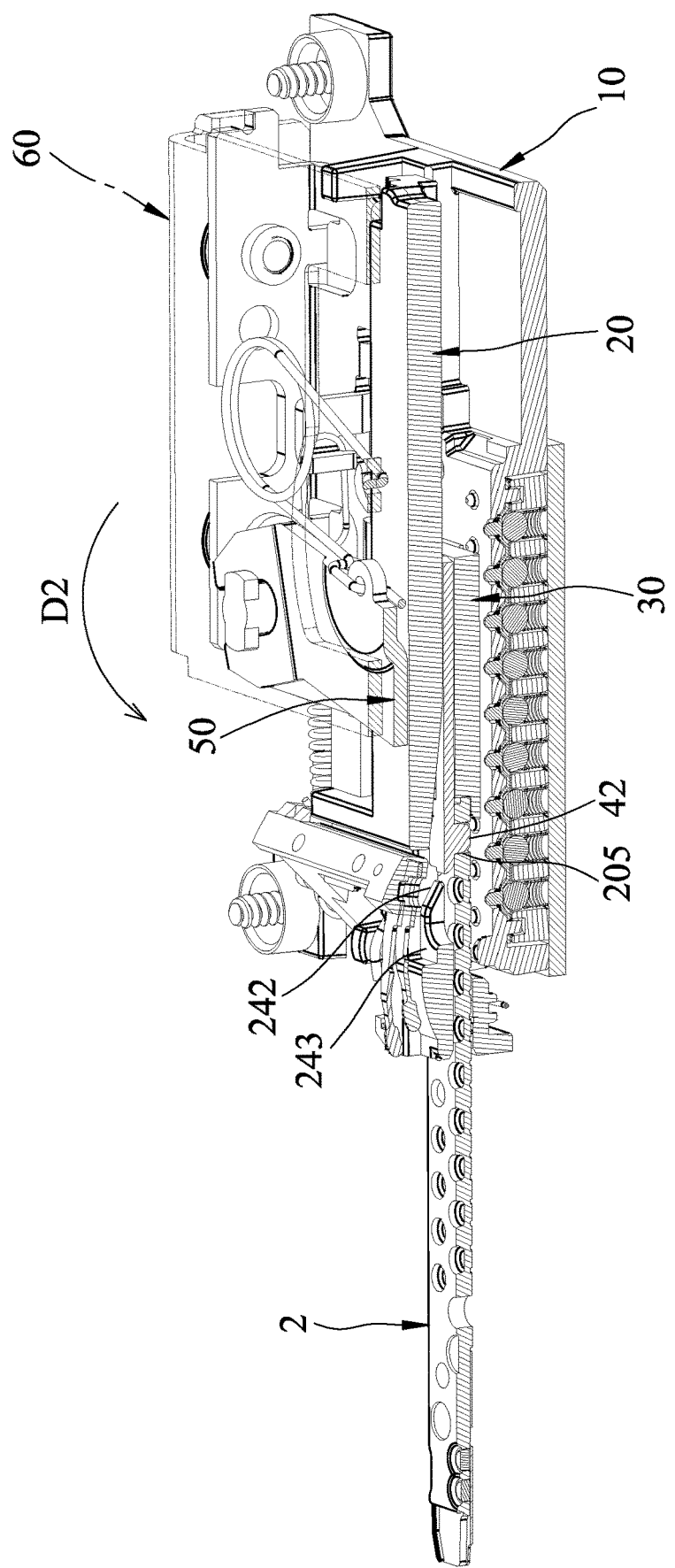
FIG. 26 is a partially cutaway perspective view of the first embodiment shown in FIG. 25.

Referring to FIG. 25 and FIG. 26, when the actuating unit 60 is at the ejecting position and the user has not yet release the eject button, the biosensor strip is at a position where approximately ¼ of the biosensor strip 2 is still in the insertion groove 23 of the strip seat 20. At this point, the upright tab 57 of the rotating plate 50 abuts against the stop surface 614 of the actuating unit 60, pausing the rotation of the rotating plate 50, and the anchor hole 205 of the biosensor strip 2 is still engaged with the anchoring portion 42 of the anchoring member 40. As such, the biosensor strip 2 is prevented from being accidentally ejected out of the strip seat 20 by its inertia of motion.

Figure 27:
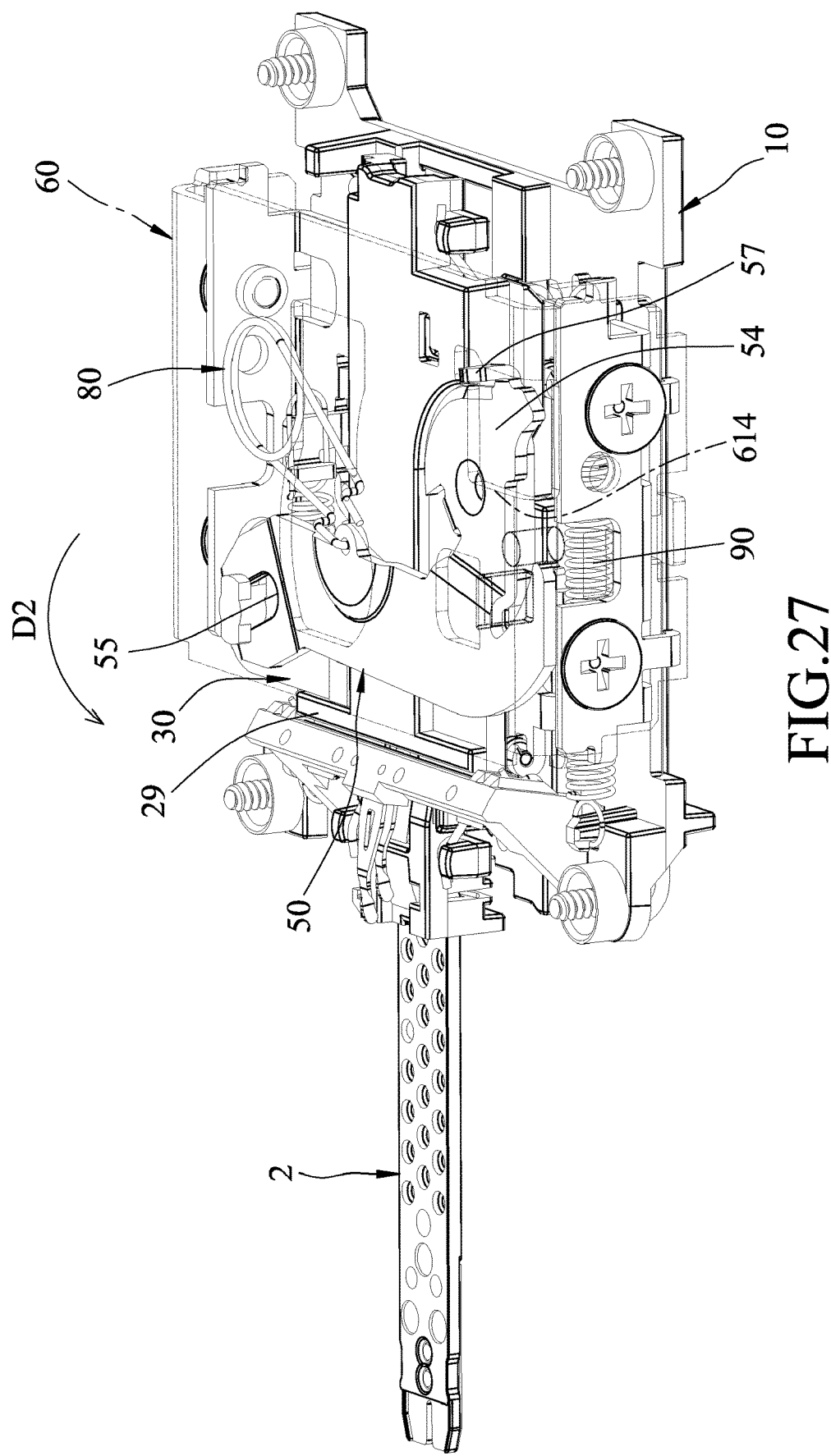
FIG. 27 is a perspective view illustrating yet another state of the first embodiment during the ejection process of the biosensor strip.
Figure 28:
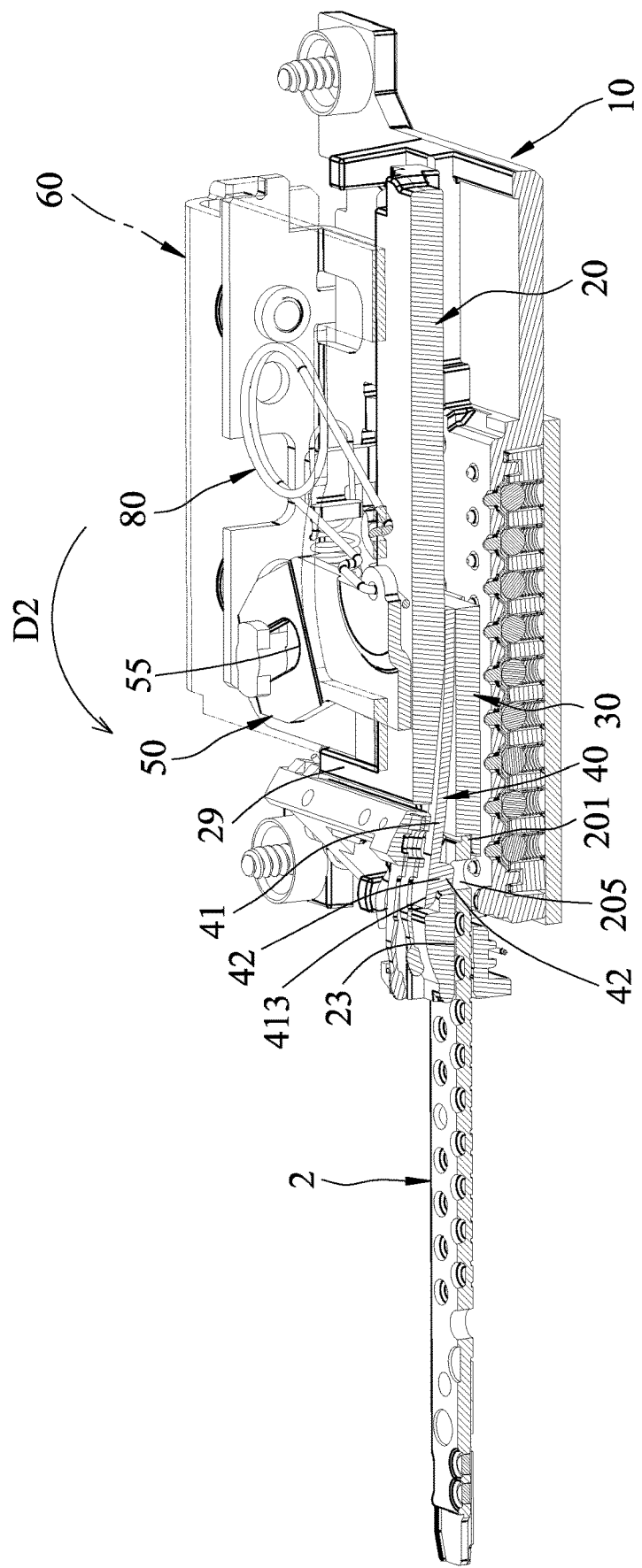
FIG. 28 is a partially cutaway perspective view of the first embodiment shown in FIG. 27.

Referring to FIGS. 27 and 28, when the user releases the eject button, the eject button and the actuating unit 60 are driven by the second driving spring 90 to move toward the first end 11 of the base body 10. During this time, the stop surface 614 of the actuating unit 60 becomes separated from the upright tab 57 of the rotating plate 50, and the rotating plate 50 is thus allowed to be driven by the first driving spring 80 to continue its rotation until the guide seat 30 is stopped by the abutment rib 29 of the strip seat 20. In the meantime, the wedge portion 413 of the anchoring member 40 is lifted by the wedge section 242 of the strip seat 20 (i.e., the swingable end 412 swings upwards and the claw portion 41 of the anchoring member 40 is bent), and the anchoring portion 42 of the anchoring member 40 disengages the positioning hole 207 of the biosensor strip 2 (see FIG. 31(d)).

Figure 29:
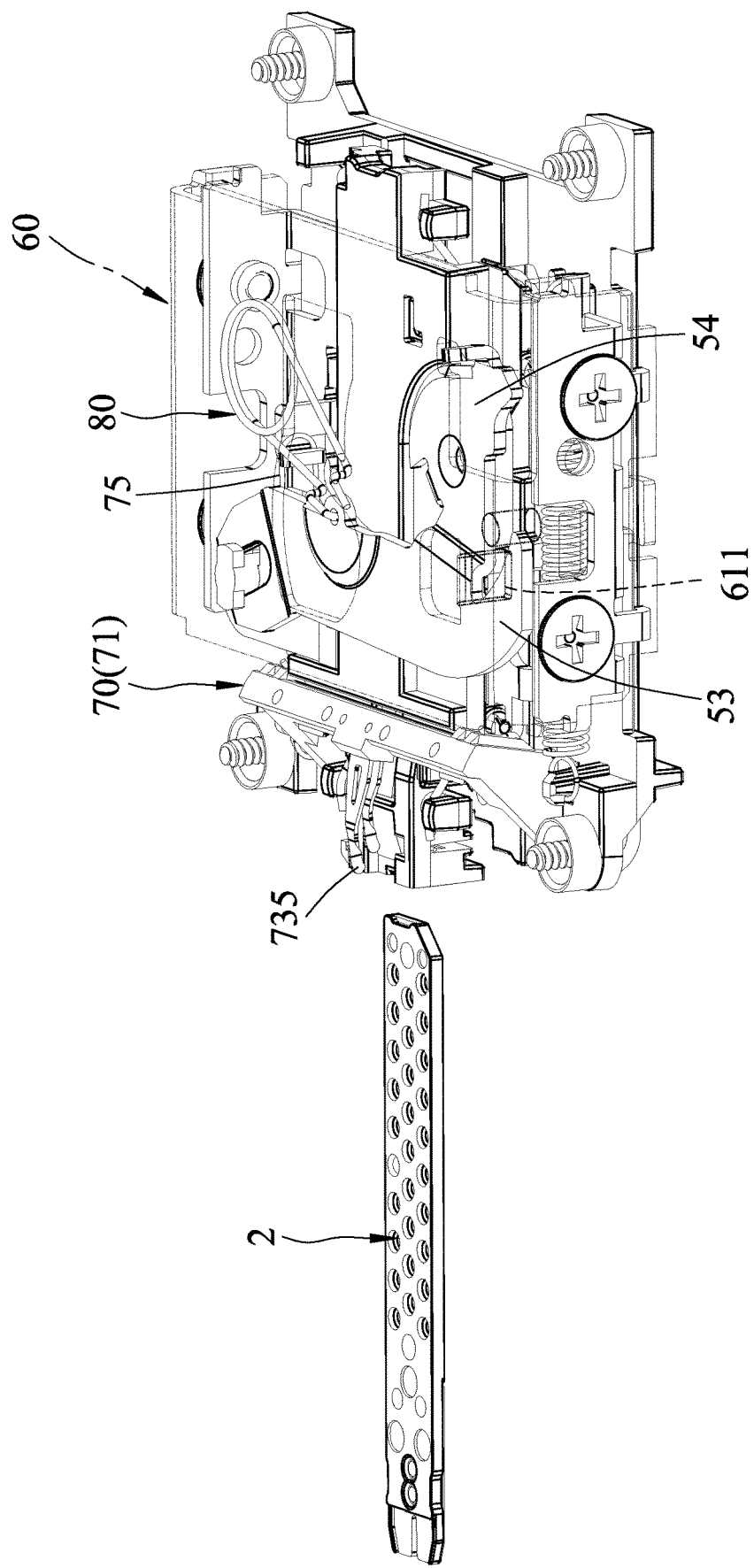
FIG. 29 is a perspective view illustrating the first embodiment when the ejection process is completed.
Figure 30:
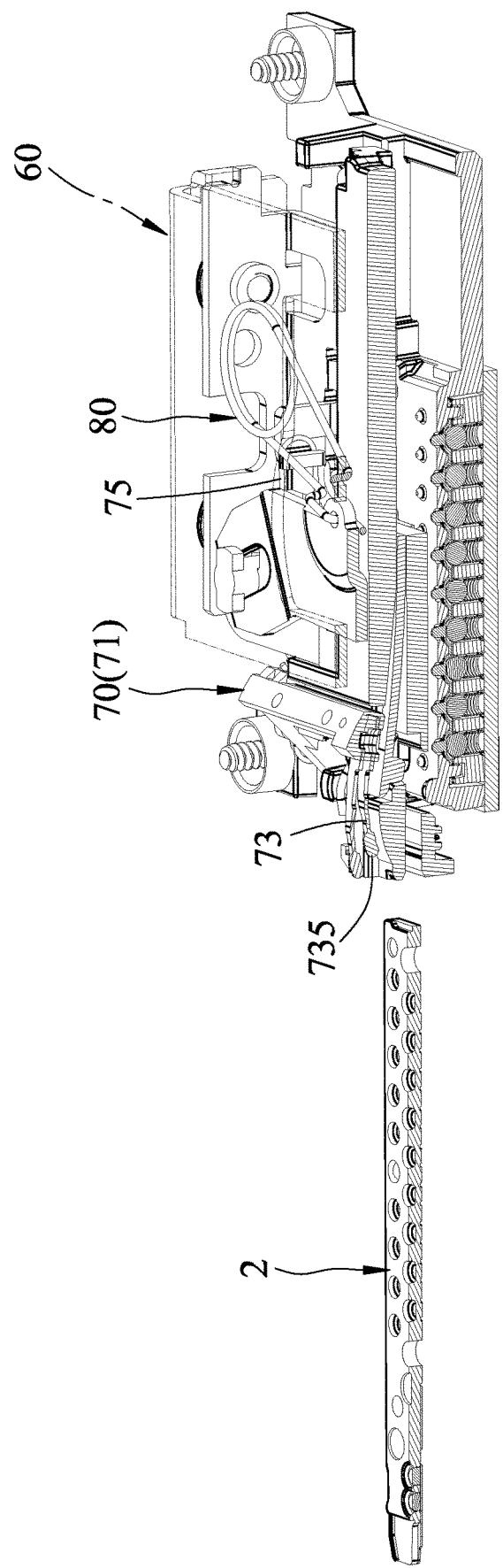
FIG. 30 is a partially cutaway perspective view illustrating the first embodiment when the ejection process is completed.

Referring to FIGS. 29 and 30, the movement of the actuating unit 60 toward the first end 11 of the base body 10 finally stops when the projecting piece 611 of the actuating unit 60 hits the hook portion 53 of the rotating plate 50. The extension spring 75 then moves slightly toward its equilibrium position and reduces its pulling force exerted onto the main body 71, allowing the main body 71 to be slightly rotated by the torsion springs 74 to bring the sliding end 735 of each of the extending pieces 73 back to the retracted position. At this point, the ejection process is completed and the biosensor strip 2 is ready to be taken out of the strip seat 20.

Figure 34:
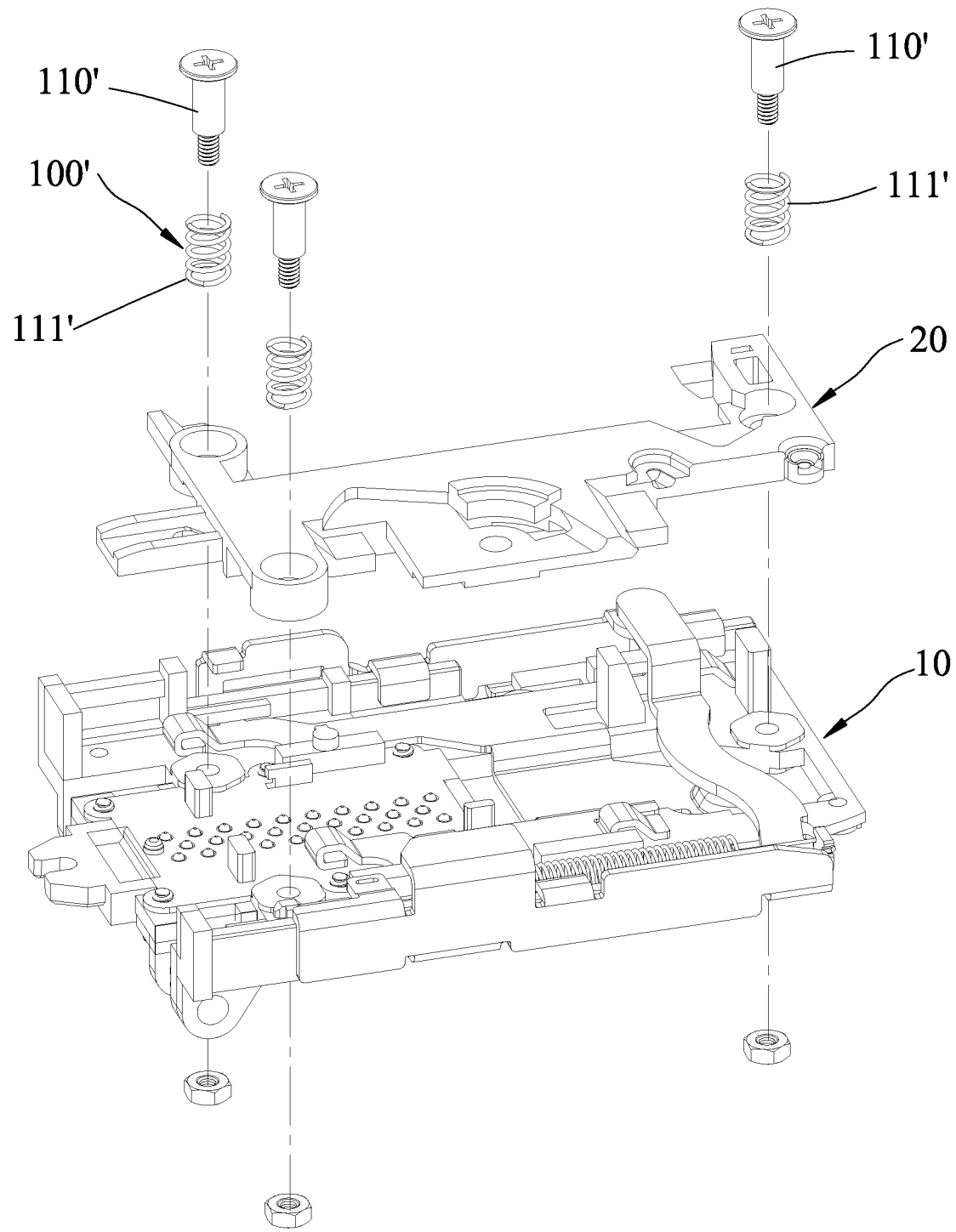
FIG. 34 is a fragmentary, partially exploded perspective view of a second embodiment of the physiological signal monitoring device according to the disclosure.

Referring to FIG. 34, a second embodiment of the physiological signal monitoring device of the disclosure is similar to the first embodiment, and the difference therebetween lies in that, in the second embodiment, the resilient unit 100' includes a plurality of screws 110' that extend through the strip seat 20 and that engage threadedly the base body 10, and a plurality of compression springs 111' that are sleeved respectively on the screws 110'. Each of the compression springs 111' has opposite ends that abut respectively against the strip seat 20 and the respective one of the screws 110'. By virtue of the disposition of the compression springs 111', the resilient unit 100' is able to drive the strip seat 20 from the upper position to the lower position when the lower driving members 631 of the actuating unit 60 (not shown in FIG. 34) are separated from the strip seat 20, providing the same function as the first embodiment.

Figure 35:
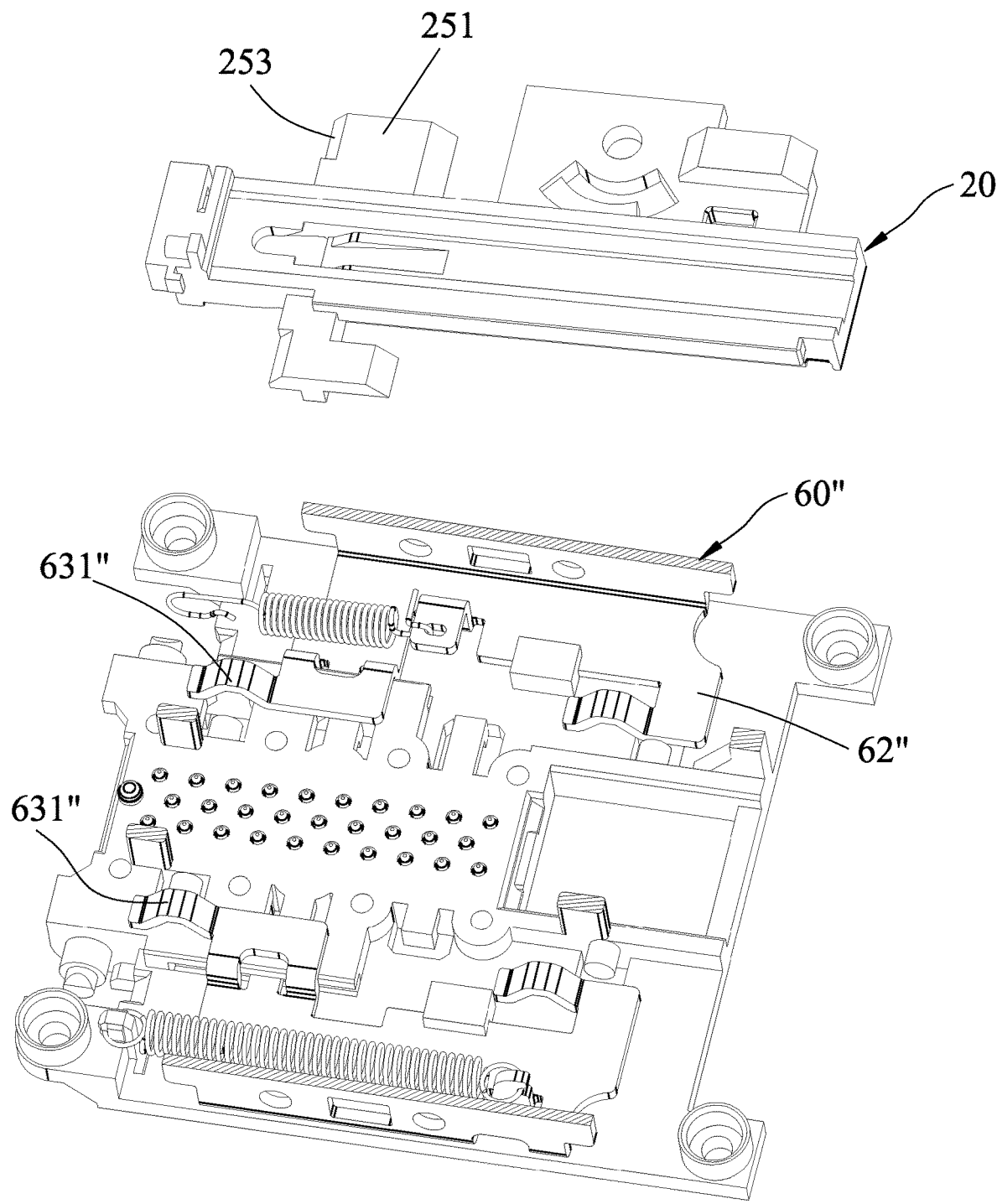
FIG. 35 is a fragmentary, partially exploded perspective view of a third embodiment of the physiological signal monitoring device according to the disclosure.

Referring to FIG. 35, a third embodiment of the physiological signal monitoring device of the disclosure is similar to the first embodiment, and the difference therebetween lies in that, in the third embodiment, each of the lower driving members 631" is a trapezoid protrusion connected to the corresponding one of the lower actuating seats 62", and corresponds in shape to the respective one of the trapezoid pieces 251. As such, the lower driving members 631" are able to slide under the trapezoid pieces 251 of the strip seat 20, respectively, to lift the strip seat 20 to the upper position, so as to provide the same function as the first embodiment.

In summary, structural features of the disclosed embodiments of the physiological signal monitoring device and their corresponding benefits are listed as follows.

1. By virtue of the disposition and design of the fool-proof groove 26 and the fool-proof spring 261 of the strip seat 20, the biosensor strip 2 is prevented from being inserted in the wrong orientation.
2. By virtue of the engagement between the guide seat 30 and the anchoring member 40 that allows the guide seat 30 and the anchoring member 40 to be configured as separate components yet still provide the desired structural flexibility within limited space, molding design of the components is simplified and production and manufacturing costs may be reduced.
3. By virtue of the configurations of the rotating plate 50 and the guide seat 30 and the engagement therebetween, the rotation of the rotating plate 50 can be converted to the linear motion of the guide seat 30 to result in a more efficient use of space for the insertion and ejection of the biosensor strip 2. In addition, in virtue of the disposition of the abutment rib 29 provided for the guide seat 30 to abut thereagainst, the rotating plate 50 is ensured to return to the original position with accuracy.
4. By virtue of the configurations of the upright tab 57 of the rotating plate 50 and the stop surface 614 of the actuating unit 60, the rotation of the rotating plate 50 is paused to keep the engagement between the anchoring portion 42 of the anchoring member 40 and the anchor hole 205 of the biosensor strip 2 near the end of ejection process, and to keep the biosensor strip 2 from being accidentally ejected out of the strip seat 20 by its inertia of motion.
5. By virtue of the position-limiting effect of the guide poles 17 of the base body 10, upward and downward movement of the strip seat 20 relative to the base body 10 is maintained with accuracy.
6. When the insertion process is completed, the engagement between the positioning pole 13 of the base body 10 and the positioning hole 207 of the biosensor strip 2 is able to prevent the biosensor strip 2 from being accidentally pulled out with force.
7. By virtue of the manufacturing methods of the main body 71, the metallic conducting pieces 72 and the extending piece 73 (the main body 71 is formed by plastic injection molding with the metallic conducting pieces 72 embedded therein, and the metallic conducting pieces 72 and the extending pieces 73 are formed as one piece by stamping sheet-like or reel-like stainless steel or copper), the two metallic conducting pieces 72 (or the two extending pieces 73) are ensured to be spaced apart from each other and are provided with great structural strength.
8. By virtue of the slots 734 and the overall configuration and material property of the extending pieces 73, the extending pieces 73 are provided with great structural strength and rigidity, the connections between each of the sliding ends 735 of the extending pieces 73 and the respective signal output ends 204 of the biosensor strip 2 are ensured.
9. A sleeve structure (surrounding a fastener) at each of the four corners of the base body 10 allows the base body 10 to be installed in the housing units of different shapes and models with ease, providing great flexibility for the design of the housing unit.
10. Finally, by virtue of the torsion springs 74 and the configuration of the extending pieces 73, the sliding ends 735 are able to remove any potential oxide layer, passivation layer or foreign objects, thereby avoiding contact interference and ensuring electrical conduction between the extending pieces 73 and the signal output ends 204.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A physiological signal monitoring device adapted for monitoring a physiological signal of a biofluid, said physiological signal monitoring device comprising:

a biosensor strip having at least one signal output end that is adapted for outputting the physiological signal;

a strip reciprocating module including
a strip seat that is configured for receiving said biosensor strip,
a guide seat that is mounted movably to said strip seat, and
a rotating plate that is mounted rotatably to said strip seat, rotation of said rotating plate triggering reciprocating movement of said biosensor strip and said guide seat relative to said strip seat; and a contact module including an electronic module, and
at least one extending piece that is electrically connected with said at least one signal output end to transmit the physiological signal to said electronic module.

2. The physiological signal monitoring device as claimed in claim 1, wherein:
said strip reciprocating module further includes
a base body, said contact module being mounted to said base body,
an anchoring member mounted on said guide seat, and
an actuating unit mounted movably to said base body, and configured to drive said contact module to pivot relative to said base body;
said physiological signal monitoring device further comprising a first driving spring, and a second driving spring;
during insertion of said biosensor strip into said physiological signal monitoring device, said guide seat is pushed by said biosensor strip to move rearwardly along an axis which extends in a front-rear direction such that the rearward movement of said guide seat drives said rotating plate to rotate in a first rotational direction;
the rotation of said rotating plate actuates operation of said first driving spring and said second driving spring to provide forward movement of said actuating unit along an axis which extends in the front-rear direction to a securing position to move said strip seat downwardly along an axis which extends in a top-bottom direction perpendicular to the front-rear direction to a lower position for electrically connecting said biosensor strip to said electronic module; and
the forward movement of said actuating unit drives said contact module to pivot for contacting said biosensor strip.

3. The physiological signal monitoring device as claimed in claim 2, wherein:
when said biosensor strip is inserted into said physiological signal monitoring device and when said actuating unit and said strip seat are respectively at the securing position and the lower position, said actuating unit is rearwardly movable to move said strip seat upwardly, and to drive said contact module to pivot away from said biosensor strip;
the rearward movement of said actuating unit drives rotation of said rotating plate in a second rotational direction which is opposite to the first rotational direction, and drives forward movement of said guide seat and said anchoring member; and
the rotation of said rotating plate in the second rotational direction actuates operation of said first driving spring to drive said rotating plate to rotate further in the second rotational direction, and to push said guide seat and said anchoring member to move forwardly further for further drawing said biosensor strip forwardly.

4. The physiological signal monitoring device as claimed in claim 2, wherein:
said electronic module is mounted to said base body;
said strip seat is downwardly and upwardly movable, and has an insertion groove for insertion of said biosensor strip thereinto, and a driven set disposed outside of said insertion groove;
said guide seat is forwardly and rearwardly movable relative to said strip seat, and has a first coupling portion;
said anchoring member is co-movable with said guide seat relative to said strip seat, and has an anchoring portion for securing said biosensor strip when said guide seat and said anchoring member are moved rearwardly by said biosensor strip during insertion of the biosensor strip;
said rotating plate has a second coupling portion coupled to said first coupling portion of said guide seat, and is rotatable between an original position and a rotated position, the rearward movement of said guide seat during insertion of said biosensor strip drives said rotating plate to rotate in the first rotational direction from the original position to the rotated position;
said actuating unit is movable along the axis which extends in the front-rear direction relative to said base body, is at an initial position when said rotating plate is at the original position, and is at the securing position when said rotating plate is at the rotated position;
said actuating unit has a driving set;
when said actuating unit is moved from the initial position to the securing position, said driven set of said strip seat is driven by said driving set of said actuating unit to move downwardly, thereby moving said strip seat downwardly from an upper position to the lower position, so that said biosensor strip inserted into said strip seat is in contact with the electronic module;
said contact module is separated from said biosensor strip when said actuating unit is at the initial position, and is in contact with said biosensor strip for electrically connecting said biosensor strip to said electronic module when said actuating unit is at the securing position;
said first driving spring is connected between said rotating plate and said actuating unit;
the rotation of said rotating plate in the first rotational direction from the original position to the rotated position actuates operation of said first driving spring to move said actuating unit from the initial position to the securing position;
the rearward movement of said actuating unit from the securing position to the initial position drives rotation of said rotating plate in the second rotational direction, such that said first driving spring is actuated to operate to drive said rotating plate to rotate further in the second rotational direction to the original position; and
said second driving spring is connected between said actuating unit and said base body;
when said actuating unit is moved from the securing position to an ejecting position, said second driving spring is operable for driving said actuating unit to move forwardly from the ejecting position to the initial position.

5. The physiological signal monitoring device as claimed in claim 4, further comprising a resilient unit biasing resiliently and downwardly said strip seat toward the lower position.

6. The physiological signal monitoring device as claimed in claim 5, wherein:
said resilient unit includes a plurality of torsion springs; and
each of said torsion springs has a spring body sleeved on said base body, a first leg connected to an end of said spring body and abutting against said base body, and a second leg connected to another end of said spring body and abutting against said strip seat.

7. The physiological signal monitoring device as claimed in claim 5, wherein said resilient unit includes:

a plurality of screws extending through said strip seat and engaging threadedly said base body; and a plurality of compression springs sleeved respectively on said screws, each of the compression springs having opposite ends that abut respectively against said strip seat and the respective one of said screws.

8. The physiological signal monitoring device as claimed in claim 4, wherein:

said insertion groove of said strip seat has a front end and a rear end that is opposite to said front end in the front-rear direction;

said strip seat further has a slide groove, said insertion groove and said slide groove being arranged in the top-bottom direction and being in communication with each other;

said slide groove has
- a straight section extending forwardly from said rear end of said insertion groove toward said front end of said insertion groove,
- a wedge section connected to said straight section and has a height in the top-bottom direction gradually increasing toward said front end of said insertion groove, and
- a limit section connected to said wedge section, and being adjacent to and not in direct communication with said insertion groove;

said anchoring member further has a claw portion being slidable along said slide groove, and having
- a positioning end that is secured to said guide seat,
- a swingable end that is opposite to said positioning end, and
- a wedge portion that is disposed on said swingable end;

during sliding movement of said anchoring member toward said limit section of said slide groove, said swingable end swings under guidance of said wedge section of said slide groove to withdraw said anchoring portion from said insertion groove; and said anchoring portion of said anchoring member is a protrusion protruding from said claw portion.

9. The physiological signal monitoring device as claimed in claim 4, wherein:

said biosensor strip further has a fool-proof edge of; and
said strip seat further has
- a fool-proof groove being adjacent to and in communication with said front end of said insertion groove, and
- a fool-proof spring inserted into said front end of said insertion groove, and configured to be resiliently pushed out of said front end of said insertion groove into said fool-proof groove by said fool-proof edge of said biosensor strip during the insertion of said biosensor strip into said insertion groove.

10. The physiological signal monitoring device as claimed in claim 4, wherein:

said strip seat further has a first engaging member extending in the front-rear direction;

said guide seat further has a second engaging member engaging said first engaging member;

said first coupling portion of said guide seat is T-shaped; and said second coupling portion of said rotating plate is a U-shaped groove engaged rotatably and slidably with said first coupling portion.

11. The physiological signal monitoring device as claimed in claim 10, wherein:

said strip seat further has an engaging hole, an arc groove around said engaging hole, and a stop piece disposed in said arc groove; and said rotating plate further has an engaging member rotatably engaging said engaging hole, and a bent piece extending into said arc groove and engaging said stop piece to restrain upward and downward movement of said rotating plate along an axis which extends in the top-bottom direction.

12. The physiological signal monitoring device as claimed in claim 4, wherein:

said rotating plate further has a hook portion opposite to said second coupling portion;

said actuating unit further has a projecting piece projecting toward said base body; and said projecting piece engages said hook portion when said actuating unit is at the initial position.

13. The physiological signal monitoring device as claimed in claim 12, wherein:

said rotating plate further has an abutment portion;

said actuating unit further has a projecting pin projecting toward said base body; and during ejection of said biosensor strip, said projecting pin of said actuating unit abuts against said abutment portion of said rotating plate such that rearward movement of said actuating unit drives said rotating plate to rotate in the second rotational direction.

14. The physiological signal monitoring device as claimed in claim 13, wherein:

said rotating plate further has a first connecting hole disposed between said hook portion and said second coupling portion;

said actuating unit further has a second connecting hole; and said first driving spring is a torsion spring, and has a spring body, and two legs connected respectively to opposite ends of said spring body and engaging respectively said first and second connecting holes.

15. The physiological signal monitoring device as claimed in claim 4, wherein:

said driven set of said strip seat has a plurality of trapezoid pieces, each having a bottom surface that faces said base body, and two inclined surfaces that are opposite to each other in the front-rear direction and that are connected respectively to opposite ends of said bottom surface;

said actuating unit includes an upper actuating seat, and two lower actuating seats connected to said upper actuating seat and connected between said base body and said strip seat; and said driving set has a plurality of lower driving members connected to said lower actuating seats and being proximate to a corresponding one of said trapezoid pieces.

16. The physiological signal monitoring device as claimed in claim 15, wherein each of said lower driving members is a roller.

17. The physiological signal monitoring device as claimed in claim 15, wherein each of said lower driving members is a protrusion and corresponds in shape to said trapezoid pieces.

18. The physiological signal monitoring device as claimed in claim 4, wherein:

said biosensor strip further has a positioning hole; and said base body has a first end, a second end opposite to said first end in the front-rear direction, and a positioning pole disposed on said first end and configured for engaging said positioning hole of said biosensor strip when said strip seat is at the lower position.

19. The physiological signal monitoring device as claimed in claim 4, wherein said contact module has:
a main body made of an insulating material, and having two swing arms that are pivoted to said base body, and a linking rod that interconnecting said swing arms;
two metallic conducting pieces embedded in said main body, being electrically conductive, and being spaced apart from each other, each of said metallic conducting pieces having a contact portion that projects out of said main body;
two extending pieces electrically and respectively connected to said metallic conducting pieces and extending out of said main body; and
two torsion springs, each having a leg that is configured to be connected electrically to said electronic module, and another leg that is connected electrically to said contact portion of a respective one of said metallic conducting pieces; and
said torsion springs is disposed for biasing said main body toward said biosensor strip to thereby ensure contact between said contact portions of said metallic conducting pieces and said biosensor strip when said actuating unit is at the initial position.

20. The physiological signal monitoring device as claimed in claim 19, wherein each of said extending pieces has a base portion connected to the respective one of said metallic conducting pieces, an extending portion configured to be in contact with said biosensor strip, and a connecting portion interconnecting said base portion and said extending portion, said base portion being formed with a slot.

21. A physiological signal monitoring device adapted for monitoring a physiological signal of a biofluid, said physiological signal monitoring device comprising:
a biosensor strip having at least one signal output end that is adapted for outputting the physiological signal;
a strip reciprocating module including
a base body,
a strip seat that is mounted to said base body, and that is configured for receiving said biosensor strip,
a guide seat that is mounted movably to said strip seat,
a rotating plate that is mounted rotatably to said strip seat, rotation of said rotating plate triggering reciprocating movement of said biosensor strip and said guide seat relative to said strip seat, and
an actuating unit that is mounted movably to said base body; and
a contact module mounted to said base body, being drivable by said actuating unit, and including
an electronic module, and
an extending piece that is electrically connected with said at least one signal output end to transmit the physiological signal to said electronic module.

22. A physiological signal monitoring device adapted for monitoring a physiological signal of a biofluid, said physiological signal monitoring device comprising:
a biosensor strip having at least one signal output end that is adapted for outputting the physiological signal;
a strip reciprocating module including
a base body,
a strip seat that is mounted to said base body, that is configured for receiving said biosensor strip, and that includes a driven set,
a guide seat that is mounted movably to said strip seat,
a rotating plate that is mounted rotatably to said strip seat, rotation of said rotating plate triggering reciprocating movement of said biosensor strip and said guide seat relative to said strip seat, and
an actuating unit that is mounted movably to said base body, and that includes a driving set,
wherein when said actuating unit is moved from the initial position to the securing position, said driven set of said strip seat is driven by said driving set of said actuating unit to move downwardly, thereby moving said strip seat downwardly from an upper position to the lower position, so that said biosensor strip inserted into said strip seat is in contact with said electronic module; and
a contact module mounted to said base body, drivable by said actuating unit, and including
an electronic module, and
an extending piece that is electrically connected with said at least one signal output end to transmit the physiological signal to said electronic module.

* * * * *